United States Patent
Mueller et al.

(10) Patent No.: US 12,138,459 B2
(45) Date of Patent: *Nov. 12, 2024

(54) ELECTRODE POSITION DETECTION

(71) Applicant: Medtronic, Inc., Minneapolis, MN (US)

(72) Inventors: Jerel K. Mueller, St. Paul, MN (US); Andrew J. Cleland, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,444

(22) Filed: Jan. 13, 2023

(65) Prior Publication Data
US 2023/0191132 A1    Jun. 22, 2023

Related U.S. Application Data

(62) Division of application No. 16/858,030, filed on Apr. 24, 2020, now Pat. No. 11,554,264.

(51) Int. Cl.
*A61N 1/05* (2006.01)
*A61M 1/36* (2006.01)
*A61N 1/36* (2006.01)

(52) U.S. Cl.
CPC ....... *A61N 1/36139* (2013.01); *A61N 1/0529* (2013.01); *A61N 1/0551* (2013.01);
(Continued)

(58) Field of Classification Search
CPC .............. A61N 1/36139; A61N 1/0529; A61N 1/0551; A61N 1/0587; A61N 1/36062;
(Continued)

(56) References Cited

U.S. PATENT DOCUMENTS 5,306,292 A    4/1994 Lindegren
5,626,629 A    5/1997 Faltys et al.
(Continued)

FOREIGN PATENT DOCUMENTS

CN    106823139 A    6/2017
EP    1181951 B1    3/2004
(Continued)

OTHER PUBLICATIONS

"Arrhythmia: Heart Palpitations." Cleveland Clinic, http://my.clevelandclinic.org/heart/disorders/electric/palpitations.aspx, captured Mar. 5, 2010, 2 pp.
(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

Devices, systems, and techniques include determining spatial relationships between electrodes implanted within a patient. In one example, a medical device delivers, via a first electrode, an electrical stimulus and senses, for each other electrode, a respective electrical signal indicative of the electrical stimulus. The medical device determines, for each other electrode, a respective value for each respective electrical signal. The medical device determines, based on the respective values for each respective electrical signal and values of tissue conductivity of tissues of the patient interposed between the first electrode and the other electrodes, spatial relationships between the first electrode and each other electrode of the plurality of electrodes.

20 Claims, 8 Drawing Sheets

(52) U.S. Cl.
CPC ....... *A61N 1/0587* (2013.01); *A61N 1/36062* (2017.08); *A61N 1/36185* (2013.01); *A61N 1/36189* (2013.01)

(58) Field of Classification Search
CPC ............ A61N 1/36185; A61N 1/36189; A61N 1/0553; A61N 1/0556; A61N 1/36003; A61N 1/36103; A61N 1/3616; A61N 1/37247; A61N 1/36007; A61N 1/36067; A61N 1/36071; A61N 1/36171; A61N 1/36175; A61N 1/3605; A61N 1/36064; A61N 1/36146; A61N 1/372; A61N 1/0534; A61N 1/36057; A61N 1/3615; A61N 1/36528; A61N 1/36535; A61N 1/37235; A61N 1/0452; A61N 1/0531; A61N 1/0539; A61N 1/3601; A61N 1/36053; A61N 1/3606; A61N 1/36082; A61N 1/36096; A61N 1/3611; A61N 1/36114; A61N 1/36132; A61N 1/3614; A61N 1/36157; A61H 1/0237; A61H 1/0274

See application file for complete search history.

(56) References Cited

U.S. PATENT DOCUMENTS

| | | | |
|---|---|---|---|
| 5,775,331 | A | 7/1998 | Raymond et al. |
| 5,928,272 | A | 7/1999 | Adkins et al. |
| 6,259,945 | B1 | 7/2001 | Epstein et al. |
| 6,393,325 | B1 | 5/2002 | Mann et al. |
| 6,473,644 | B1 | 10/2002 | Terry, Jr. et al. |
| 6,587,724 | B2 | 7/2003 | Mann |
| 6,622,048 | B1 | 9/2003 | Mann et al. |
| 6,640,136 | B1 | 10/2003 | Helland et al. |
| 6,731,986 | B2 | 5/2004 | Mann |
| 7,065,412 | B2 | 6/2006 | Swoyer et al. |
| 7,104,965 | B1 | 9/2006 | Jiang et al. |
| 7,174,215 | B2 | 2/2007 | Bradley |
| 7,254,446 | B1 | 8/2007 | Erickson et al. |
| 7,317,944 | B1 | 1/2008 | Overstreet |
| 7,317,948 | B1 | 1/2008 | King et al. |
| 7,499,752 | B2 | 3/2009 | Machino et al. |
| 7,519,431 | B2 | 4/2009 | Goetz et al. |
| 7,567,840 | B2 | 7/2009 | Armstrong |
| 7,578,819 | B2 | 8/2009 | Bleich et al. |
| 7,643,881 | B2 | 1/2010 | Armstrong |
| 7,689,286 | B2 | 3/2010 | Pastore et al. |
| 7,711,419 | B2 | 5/2010 | Armstrong et al. |
| 8,233,992 | B2 | 7/2012 | Zhu et al. |
| 8,401,665 | B2 | 3/2013 | Bradley et al. |
| 8,412,345 | B2 | 4/2013 | Moffitt |
| 8,913,804 | B2 | 12/2014 | Blum et al. |
| 8,918,184 | B1 | 12/2014 | Torgerson et al. |
| 9,089,705 | B2 | 7/2015 | Zhu |
| 9,403,020 | B2 | 8/2016 | Wingeier |
| 9,446,243 | B2 | 9/2016 | Marnfeldt et al. |
| 9,649,494 | B2 | 5/2017 | Gerber et al. |
| 9,789,307 | B2 | 10/2017 | Gerber et al. |
| 10,213,148 | B2 | 2/2019 | Min et al. |
| 10,420,940 | B2 | 9/2019 | Moffitt |
| 10,448,889 | B2 | 10/2019 | Gerber et al. |
| 10,485,970 | B2 | 11/2019 | Gerber et al. |
| 11,554,264 | B2 | 1/2023 | Mueller et al. |
| 2002/0072770 | A1 | 6/2002 | Pless |
| 2003/0040676 | A1 | 2/2003 | Prentice et al. |
| 2003/0073899 | A1 | 4/2003 | Ruohonen et al. |
| 2003/0153959 | A1 | 8/2003 | Thacker et al. |
| 2004/0116978 | A1 | 6/2004 | Bradley |
| 2004/0158298 | A1 | 8/2004 | Gliner et al. |
| 2004/0167586 | A1 | 8/2004 | Overstreet |
| 2005/0107654 | A1 | 5/2005 | Riehl |
| 2005/0119714 | A1 | 6/2005 | Sieracki et al. |
| 2005/0222626 | A1 | 10/2005 | DiLorenzo |
| 2005/0245987 | A1 | 11/2005 | Woods et al. |
| 2006/0074450 | A1 | 4/2006 | Boveja et al. |
| 2006/0085048 | A1 | 4/2006 | Cory et al. |
| 2006/0167498 | A1 | 7/2006 | DiLorenzo |
| 2006/0173510 | A1 | 8/2006 | Besio et al. |
| 2006/0195159 | A1 | 8/2006 | Bradley et al. |
| 2006/0229677 | A1 | 10/2006 | Moffitt et al. |
| 2006/0253174 | A1 | 11/2006 | King |
| 2007/0016097 | A1 | 1/2007 | Farquhar et al. |
| 2007/0043395 | A1 | 2/2007 | Wei et al. |
| 2007/0100389 | A1 | 5/2007 | Jaax et al. |
| 2007/0219452 | A1* | 9/2007 | Cohen ...................... A61B 5/24 600/509 |
| 2007/0233194 | A1 | 10/2007 | Craig |
| 2007/0255320 | A1 | 11/2007 | Inman et al. |
| 2008/0027514 | A1 | 1/2008 | DeMulling et al. |
| 2008/0086175 | A1 | 4/2008 | Libbus et al. |
| 2008/0147140 | A1 | 6/2008 | Ternes et al. |
| 2008/0234780 | A1 | 9/2008 | Smith et al. |
| 2008/0269812 | A1 | 10/2008 | Gerber et al. |
| 2008/0281381 | A1 | 11/2008 | Gerber et al. |
| 2009/0030493 | A1 | 1/2009 | Colborn et al. |
| 2009/0043352 | A1 | 2/2009 | Brooke et al. |
| 2009/0076561 | A1 | 3/2009 | Libbus et al. |
| 2009/0112281 | A1 | 4/2009 | Miyazawa et al. |
| 2009/0198294 | A1 | 8/2009 | Rossing et al. |
| 2009/0299214 | A1 | 12/2009 | Wu et al. |
| 2010/0010383 | A1 | 1/2010 | Skelton et al. |
| 2010/0010390 | A1 | 1/2010 | Skelton et al. |
| 2010/0010576 | A1 | 1/2010 | Skelton et al. |
| 2010/0010580 | A1 | 1/2010 | Skelton et al. |
| 2010/0010584 | A1 | 1/2010 | Skelton et al. |
| 2010/0010585 | A1 | 1/2010 | Davis et al. |
| 2010/0010586 | A1 | 1/2010 | Skelton et al. |
| 2010/0030299 | A1 | 2/2010 | Covalin |
| 2010/0114192 | A1 | 5/2010 | Jaax et al. |
| 2010/0114204 | A1 | 5/2010 | Burnes et al. |
| 2010/0114221 | A1 | 5/2010 | Krause et al. |
| 2010/0121408 | A1 | 5/2010 | Imran et al. |
| 2010/0161007 | A1 | 6/2010 | King |
| 2010/0249875 | A1 | 9/2010 | Kishawi et al. |
| 2010/0262209 | A1 | 10/2010 | King et al. |
| 2011/0046506 | A1 | 2/2011 | Durand et al. |
| 2011/0270119 | A1 | 11/2011 | Rasmussen |
| 2011/0270357 | A1 | 11/2011 | Torgerson et al. |
| 2011/0276107 | A1 | 11/2011 | Simon et al. |
| 2012/0101537 | A1* | 4/2012 | Peterson ............ A61N 1/36185 607/2 |
| 2012/0109004 | A1 | 5/2012 | Cadwell |
| 2012/0271382 | A1 | 10/2012 | Arcot-Krishnamurthy et al. |
| 2012/0277621 | A1 | 11/2012 | Gerber et al. |
| 2013/0006324 | A1* | 1/2013 | Bradley ................ A61N 1/0551 607/45 |
| 2019/0240489 | A1 | 8/2019 | Tsay et al. |
| 2020/0029894 | A1 | 1/2020 | Gerber et al. |
| 2020/0046970 | A1 | 2/2020 | Gerber et al. |

FOREIGN PATENT DOCUMENTS

| | | |
|---|---|---|
| WO | 2004064634 A1 | 8/2004 |
| WO | 2006073393 A1 | 7/2006 |
| WO | 2009134478 A1 | 11/2009 |
| WO | 2009158389 A1 | 12/2009 |
| WO | 2010065146 A1 | 6/2010 |
| WO | 2010105261 A1 | 9/2010 |

OTHER PUBLICATIONS

"Bradycardia (Slow Heart Rate)—Overview". WebMD, http://www.webmd.com/heart-disease/tc/bradycardia-slow-heart-rate-overview, captured Jan. 30, 2010, updated Jun. 18, 2009, 2 pp.

Glerum et al., "Influence of Various Electrodes and Tissues on the Electrical Impedance of Woody Stems", can. J. Plant Sci, 53, 1973, pp. 385-389 (Applicant points out, in accordance with MPEP 609.04(a), that the year of publication, 1973, is sufficiently earlier than the effective U.S. filing date, so that the particular month of publication is not in issue.).

(56) References Cited

OTHER PUBLICATIONS

International Preliminary Report on Patentability from International Application No. PCT/US2021/028159 dated Nov. 3, 2022, 7 pp.
International Search Report and Written Opinion of International Application No. PCT/US2021/028159, dated Aug. 30, 2021, 10 pp.
International Search Report and Written Opinion of International Application No. PCT/US2021/028159, mailed Aug. 30, 2021, 19 pp.
Prosecution History from U.S. Appl. No. 16/858,030m now issued U.S. Pat. No. 11,554,264, dated Jul. 20, 2021 through Dec. 21, 2022, 57 pp.
Schachter et al., "Warning Signs of Seizures," Aug. 2013, Epilepsy Foundation, retrieved from internet www.epilepsy.com/get-help/managing-you-epilepsy/understanding-seizures-and-emergencies/warning-signs-seizures on Sep. 30, 2014, 2 pp.
U.S. Appl. No. 61/480,864, by Gerber et al., filed on Apr. 29, 2011.
U.S. Appl. No. 61/480,887, by Gerber et al., filed on Apr. 29, 2011.
U.S. Appl. No. 61/480,928, by Gerber et al., filed on Apr. 29, 2011.

\* cited by examiner

ELECTRODE POSITION DETECTION

This application is a divisional application claiming priority to U.S. patent application Ser. No. 16/858,030, filed Apr. 24, 2020, now U.S. Pat. No. 11,554,264 B2, the entire contents of which is incorporated herein by reference.

TECHNICAL FIELD

This disclosure generally relates to medical therapy and, more particularly, electrical stimulation therapy.

BACKGROUND

Medical devices, including implantable medical devices (IMDs), may be used to treat a variety of medical conditions. Medical electrical stimulation devices, for example, may deliver electrical stimulation therapy to a patient via external and/or implanted electrodes. Electrical stimulation therapy may include stimulation of nerve tissue, muscle tissue, the brain, the heart, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads with percutaneous lead extensions.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via leads that include electrodes implantable proximate to the spinal cord, pelvic nerves, gastrointestinal organs, sacral nerves, peripheral nerves, or within the brain of a patient. Stimulation may be delivered from electrodes implanted proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, the disclosure describes methods, devices, systems, and techniques for determining spatial relationships, such as distances, between electrodes implanted within a patient. For example, the medical device may be configured to deliver, via a first electrode of the plurality of electrodes, an electrical stimulus defined by at least one parameter. In some examples, the at least one parameter is a first voltage amplitude. The medical device may also be configured to sense, via each of the other electrodes of the plurality of electrodes, respective electrical signals indicative of the electrical stimulus. In some examples, the respective electrical signals are indicative of second voltage amplitude values sensed by each other electrode of the plurality of electrodes. The medical device can then determine, based on the respective values for each respective electrical signal sensed by each other electrode of the plurality of electrodes, spatial relationships, such as distances, of the first electrode to each of the other electrodes of the plurality of electrodes.

In some examples, the medical device may repeat the foregoing process to determine a distance between each pair of electrodes of the plurality of electrodes. The plurality of electrodes may be carried by two or more different implantable structures, such as two or more implantable medical leads.

In some examples, the medical device selects, based on the spatial relationships of the first electrode to each of the other electrodes, one or more electrodes for delivering electrical stimulation therapy and then delivers electrical stimulation therapy via the selected one or more electrodes. In other examples, the medical device may determine an amplitude or other parameter defining electrical stimulation based at least in part on a spatial relationship between two or more electrodes. In some examples, the medical device selects, based on the spatial relationships of the first electrode to each of the other electrodes, one or more electrodes for sensing a biosignal of the patient and then senses a biosignal of the patient via the selected one or more electrodes. In some examples, the medical device outputs, for display to a user, a representation of the plurality of electrodes depicting the spatial relationship between at least some of the plurality of electrodes.

In one example, a medical device senses impedances between the first electrode and each of the other electrodes. The medical device can then determine, based on the sensed impedances, a type of a tissue interposed between the first electrode to each of the other electrodes. Further, the medical device can determine, based on the type of the tissue, a tissue conductivity of the tissues interposed between the first electrode to each of the other electrodes. The medical device may use both the values of a tissue conductivity of tissues interposed between the plurality of electrodes and the respective values for each respective electrical signal sensed by each other electrode of the plurality of electrodes to determine the spatial relationships of the first electrode to each of the other electrodes of the plurality of electrodes.

In one example, this disclosure describes a method comprising: controlling, by processing circuitry of a medical device, stimulation generation circuitry to deliver, via a first electrode of a plurality of electrodes, an electrical stimulus; sensing, by sensing circuitry and for each other electrode of the plurality of electrodes, a respective electrical signal indicative of the electrical stimulus; determining, by the processing circuitry and for each other electrode, a respective value for each respective electrical signal; and determining, by the processing circuitry, and based on the respective values for each respective electrical signal sensed by each other electrode of the plurality of electrodes, spatial relationships between the first electrode and each other electrode of the plurality of electrodes.

In another example, this disclosure describes a medical device system comprising: stimulation generation circuitry configured to deliver electrical stimulation via a first electrode of a plurality of electrodes; and processing circuitry configured to control the stimulation generation circuitry to deliver, via the first electrode, an electrical stimulus; sensing circuitry configured to sense, for each other electrode of the plurality of electrodes, a respective electrical signal indicative of the electrical stimulus, wherein the processing circuitry is further configured to determine, for each other electrode, a respective value for each respective electrical signal, and wherein the processing circuitry is further configured to determine, based on the respective values for each respective electrical signal sensed by each other electrode of the plurality of electrodes, spatial relationships between the first electrode and each other electrode of the plurality of electrodes.

In another example, this disclosure describes a non-transitory computer-readable medium comprising instructions that, when executed, are configured to cause processing circuitry of a medical device to: control stimulation generation circuitry of the medical device to deliver, via a first electrode of a plurality of electrodes, an electrical stimulus; control sensing circuitry to sense, for each other electrode of the plurality of electrodes, a respective electrical signal indicative of the electrical stimulus; determine, for each other electrode, a respective value for each respective electrical signal; and determine, based on the respective values for each respective electrical signal sensed by each other electrode of the plurality of electrodes, spatial relationships between the first electrode and each other electrode of the plurality of electrodes.

In another example, this disclosure describes a method comprising: sensing, by sensing circuitry of a medical device and for each electrode of a plurality of electrodes, a respective electrical signal indicative of a cardiac signal of a heart of a patient; determining, by the processing circuitry and for each electrode of the plurality of electrodes, a respective value for each respective electrical signal; and determining, by the processing circuitry, and based on the respective values for each respective electrical signal sensed by each electrode of the plurality of electrodes, a spatial relationship between each electrode of the plurality of electrodes and the heart of the patient.

In another example, this disclosure describes a medical device system comprising: sensing circuitry of a medical device configured to sense, for each electrode of a plurality of electrodes, a respective electrical signal indicative of a cardiac signal of a heart of a patient; and processing circuitry configured to: determine, for each electrode of the plurality of electrodes, a respective value for each respective electrical signal; and determine, based on the respective values for each respective electrical signal sensed by each other electrode of the plurality of electrodes, a spatial relationship between each electrode of the plurality of electrodes and the heart of the patient.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
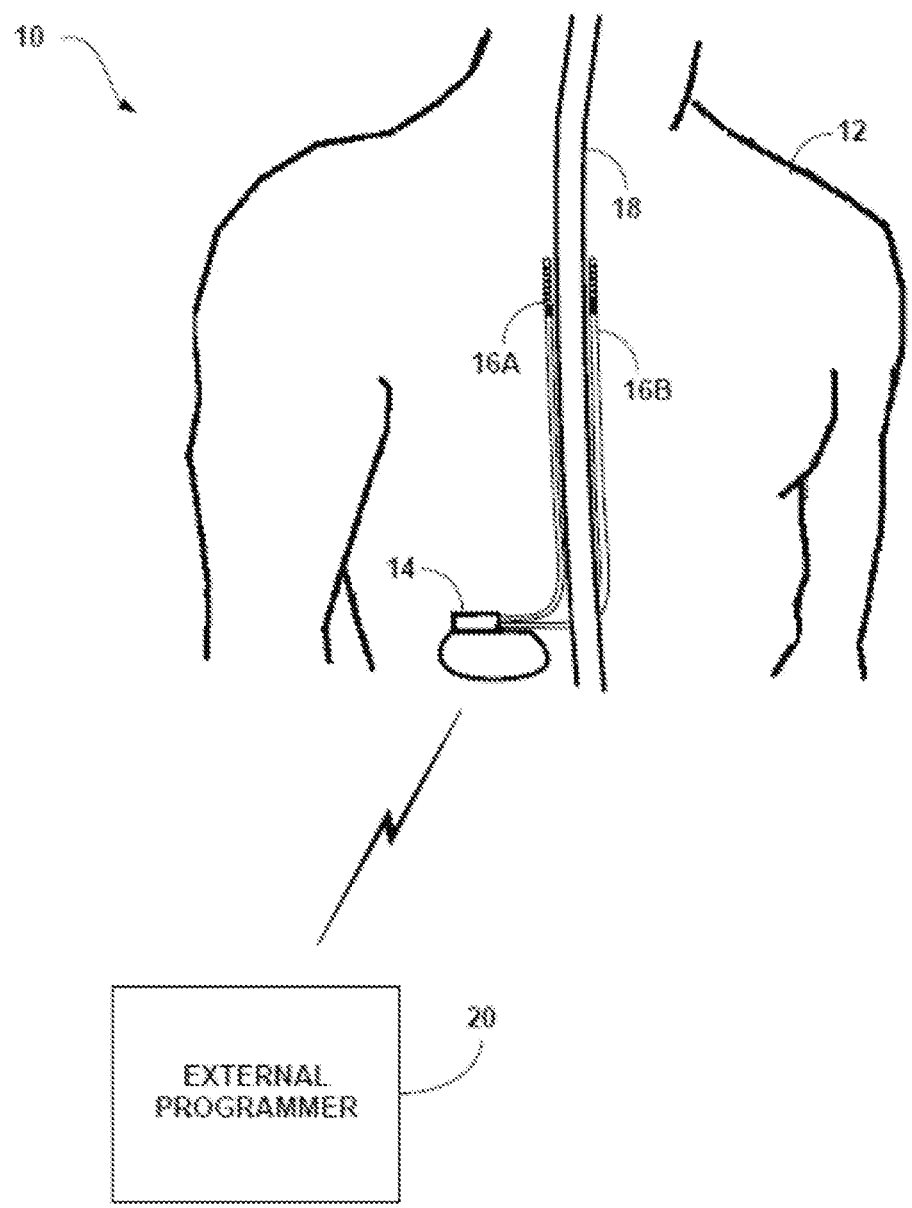
FIG. 1 is a schematic diagram illustrating an example implantable stimulation system including an implantable medical device, a pair of implantable stimulation electrode arrays carried by implantable leads, and an external programmer in accordance with the techniques of the disclosure.

This disclosure describes devices, systems, and techniques for determining spatial relationships, such as distances, between electrodes implanted within a patient. A medical device, such as an IMD or external stimulator, typically delivers electrical stimulation therapy and/or senses a biosignal of the patient via a plurality of electrodes disposed on one or more leads. The one or more leads are typically implanted in the epidural space for spinal cord stimulation, but other locations are possible for other therapies or sensing targets. The location of the electrodes carried by the one or more leads along the spinal cord directly effects the efficacy of stimulation therapy directed to nerves of the spinal cord. An implantable medical device may utilize a specific electrode combination to provide fine tuning of the shape of the electrical field produced by electrical stimulation delivered via the electrode combination selected from the plurality of electrodes.

Clinicians typically implant each lead to a desired location within the anatomy of the patient. However, the precise location of the leads with respect to each other and/or target anatomy may not result as intended by the clinician. For example, the implanted leads may not be parallel to one another and/or one or more leads may have a slight curve that affects the final location of the electrodes. Further, the leads of the medical device may shift over time, either axially or laterally within the tissue. Fluoroscopy may be capable of determining a true location of the leads, and the electrodes disposed on the leads, within the patient. However, such imaging of the leads is not a practical solution for all patients or while the patient is receiving therapy. Therefore, without knowing the location of the electrodes, efficacy of the delivered therapy may be reduced or more time may be required by the clinician to find appropriate parameters for electrical stimulation therapy using electrodes at unknown locations (e.g., by trial and error).

The techniques described herein enable a medical device to determine a spatial relationship, e.g. a distance, of each electrode to each other electrode. For example, the medical device may serially activate each electrode independently while recording from the remaining electrodes. The medical device may utilize the relative voltages recorded from each electrode to approximate the distances between each electrode. In some examples, the medical device may incorporate tissue conductivity to estimate distances between electrodes. For example, the medical device may make the assumption that the tissue of the patient between the electrodes is of a uniform type, such as the epidural space in the spinal cord, that is a consistent electrical conducting medium. The medical device may also apply an assumed known conductivity of the tissue. The medical device may store the conductivity of the tissue, e.g., the epidural space, in memory and use the conductivity to determine a relative location or distance of the electrodes with respect to one another. In other examples, the medical device may back-calculate the conductivity of the epidural space using a known contact separation distance on the same lead. In this manner, a medical device may convert a set of voltages for each electrode relative to each other electrode into a spatial relationship, such as a distance, using the assumed/calculated resistivity of the medium between them. The medical device may use the determined spatial relationships to perform other actions. As some examples, the medical device may adjust one or more parameter values in order to automate focal field targeting for electrical stimulation, compensate for lead migration, perform real-time electrical stimulation therapy parameter adjustment to keep an electrical field consistent during inter-lead movements, or provide location information to reduce the need for fluoroscopy to identify lead positions. In some other examples, the medical device or other device may use the spatial relationships between electrodes to generate a visual representation of the position of the electrodes, and/or leads upon which they are carried, with respect to each other and/or one or more anatomical structures of the patient.

The methods, devices, systems, and techniques of the disclosure may provide specific improvements to the field of electrical stimulation therapy that have practical applications. For example, the techniques described herein may enable a medical device, such as an IMD, to accurately measure distances between electrodes disposed on different leads implanted within a patient. Furthermore, the techniques described herein may enable a medical device, such as an IMD or external programmer, to generate a representation of the position of the electrodes relative to one another for display to a clinician. Such a representation may depict a position of each of the plurality of electrodes relative to one another with a high degree of accuracy. By accurately identifying the distances between multiple electrodes of leads, the techniques described herein may enable a clinician and/or a medical device to select electrodes suited for delivery of efficacious electrical stimulation therapy or sensing of biosignals from the patient, thereby increasing the efficacy of electrical stimulation therapy and/or decreasing the risk of side effects of the electrical stimulation therapy. Further, the techniques of the disclosure may enable the identification of anatomical structures within tissues of the patient, such as soft tissue structures within the patient.

FIG. 1 is a schematic diagram illustrating an example implantable stimulation system 10 including IMD 14, a pair of implantable electrode arrays in the form of stimulation leads 16A and 16B, and external programmer 20. Although the techniques described in this disclosure may be generally applicable to a variety of medical devices including external and IMDs, application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1, system 10 includes an IMD 14 and external programmer 20 shown in conjunction with a patient 12. In the example of FIG. 1, IMD 14 is an implantable electrical stimulator configured for spinal cord stimulation (SCS), e.g., for relief of chronic pain or other symptoms. Again, although FIG. 1 shows an implantable medical device, other embodiments may include an external stimulator, e.g., with percutaneously implanted leads, or implanted leads with percutaneous lead extensions. Stimulation energy is delivered from IMB 14 to spinal cord 18 of patient 12 via one or more electrodes disposed on implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1 is directed to SCS therapy, system 10 may alternatively be directed to any other condition that may benefit from stimulation therapy. For example, system 10 may be used to deliver stimulation to one or more tissues in order to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes and the parameters for a program that controls delivery of stimulation therapy by IMB 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. In some examples, leads 16, and the one or more electrodes disposed on leads 16, are implanted within an epidural space of the patient. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16, e.g., in bipolar, unipolar, or multipolar combinations. The target tissue may be any tissue affected by electrical stimulation energy, such as electrical stimulation pulses or waveforms. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which multiplexing operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead. Other electrode and lead configurations may be adapted for use with the present disclosure so long as they enable IMD 14 to electrically stimulate and sense from a target tissue.

In the example of FIG. 1, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), sacral neuromodulation (SNM), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate (i.e., pulse frequency) in the case of stimulation pulses.

In some examples, IMD 14 may deliver stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, and a pulse rate, for stimulation pulses delivered by IMD 14 according to that program. The program may also define an electrode combination for delivery of the stimulation pulse, including electrode polarities. Moreover, therapy may be delivered according to multiple programs, wherein multiple programs are contained within each of a multiple of groups.

A user, such as a clinician or patient 12, may interact with a user interface of external programmer 20 to program IMD 14. The user interface may include an output device for presentation of information, and an input device to receive user input. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A program group may be characterized by multiple programs that are delivered simultaneously or on an interleaved or rotating basis.

During the delivery of stimulation therapy, patient 12 may make patient therapy adjustments, i.e., patient adjustments to one or more parameters of a therapy via an input device of a user interface of a programmer, to customize the therapy. In examples where IMD 14 is in a record mode to store all patient therapy adjustments associated with a specific patient state, IMD 14 may implement a method to ensure that patient therapy adjustments are associated with the correct patient state intended by patient 12 when the therapy adjustment was made. The patient 12 may occupy the patient state multiple times such that there are multiple instances of the sensed patient state. A patient state may be a posture or activity level, for example. In some examples, each time the patient 12 occupies a posture state, the patient may enter one or more therapy adjustments.

In some cases, external programmer 20 may be characterized as a physician or clinician programmer if it is primarily intended for use by a physician or clinician. In other cases, external programmer 20 may be characterized as a patient programmer if it is primarily intended for use by a patient, e.g., for entry of patient input to specify patient adjustments to one or more therapy parameters. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use, either manually or via other user input media.

IMD 14 may be constructed with a biocompatible housing, such as titanium or stainless steel, or a polymeric material such as silicone or polyurethane, and surgically implanted at a site in patient 12 near the pelvis. IMB 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMB 14. Leads 16 may be tunneled from IMD 14 through tissue to reach the target tissue adjacent to spinal cord 18 for stimulation delivery.

At the distal ends of leads 16 are one or more electrodes that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes (e.g., partial ring electrodes located at different circumferential positions around the perimeter of the lead), or any other type of electrodes capable of forming unipolar, bipolar or multipolar electrode configurations for therapy. The electrodes may pierce or affix directly to the tissue itself. In general, ring electrodes arranged at different axial positions at the distal ends of leads 16 will be described for purposes of illustration.

In accordance with the techniques of the disclosure, IMD 14 determines distances between electrodes disposed on leads 16. In one example, IMB 14 senses an impedance between pairs of electrodes disposed on leads 16. IMB 14 determines, based on the sensed impedances, a type of a tissue interposed between each of the pairs of electrodes disposed on leads 16. Further, IMD 14 determines, based on the type of the tissue, a tissue conductivity of the tissue interposed between each of the pairs of electrodes disposed on leads 16.

IMD 14 delivers, via a first electrode, electrical stimulation defined by at least one parameter. In some examples, the parameter is a voltage amplitude. IMB 14 senses, via each of the other electrodes, values of the parameter of the delivered electrical stimulation. IMD 14 determines, based on the sensed values of the parameter and the values of the tissue conductivity of the tissues interposed between the electrodes, a distance of the first electrode to each of the other electrodes. In some examples, IMD 14 may repeat the foregoing process for each electrode of disposed on leads 16 to determine a distance of each electrode to each other electrode.

In some examples, IMD 14 selects, based on the distance of the first electrode to each of the other electrodes, one or more electrodes and delivers electrical stimulation therapy via the selected one or more electrodes. In some examples, IMD 14 selects, based on the distance of the first electrode to each of the other electrodes, one or more electrodes and senses a biosignal of patient 12 via the selected one or more electrodes. In this fashion, IMD 14 may select electrodes for delivery of stimulation or sensing a biosignal that are located in a desired tissue of a patient, e.g., nervous tissue. Furthermore, IMB 14 may avoid the use of electrodes for delivery of stimulation or sensing a biosignal that are located next to undesirable tissue, such as a bone tissue of the patient, which may interfere with the delivery of electrical stimulation therapy or cause erroneous measurements or artifacts during sensing. In some examples, IMD 14 outputs, for display to a user via a display device of external programmer 20, a representation of the plurality of electrodes depicting the distance of the first electrode to each of the other electrodes disposed on leads 16.

In one example, IMD 14 senses an impedance (or measures an impedance based on a sensed voltage drop) between pairs of electrodes disposed on leads 16. IMD 14 determines, based on the sensed impedances, a type of a tissue interposed between each of the pairs of electrodes disposed on leads 16. IMD 14 may use the tissue conductivity of the tissue interposed between the first electrode and each of the other electrodes as well as the respective electrical signals indicative of the electrical stimulus to determine the spatial relationship of the first electrode to each of the other electrodes.

In the aforementioned example, IMD 14 determines distances between electrodes disposed on leads 16. However, in other examples, other devices, such as external programmer 20, may receive, via telemetric communications from IMB 14, measurements sensed by IMD 14 and use such information to determines the distances between electrodes disposed on leads 16. Such devices, such as external programmer 20, may, e.g., select, based on the distance of the first electrode to each of the other electrodes, one or more electrodes and control IMD 14 to deliver electrical stimulation therapy or sense a biosignal of patient 12 via the selected one or more electrodes. In some examples, external programmer 20 may output, for display to a user, a representation of the plurality of electrodes depicting the distance of the first electrode to each of the other electrodes disposed on leads 16.

The methods, devices, systems, and techniques of the disclosure may provide specific improvements to the field of electrical stimulation therapy that have practical applications. For example, the techniques described herein may enable a medical device, such as IMD 14, to accurately measure distances between electrodes disposed on different leads implanted within a patient. IMD 14, or a user, may utilize these distances to determine appropriate electrode combinations or other parameter values (e.g., amplitude or pulse width) that define electrical stimulation deliverable to the patient. Furthermore, the techniques described herein may enable a medical device, such as IMD 14 or external programmer 20, to generate a representation of the position of the electrodes relative to one another for display to a clinician. Such a representation may depict a position of each of the plurality of electrodes relative to one another with a high degree of accuracy. This information may be helpful for identifying non-parallel leads or leads that have shifted axially within the patient, for example. By accurately identifying the distances between multiple electrodes of leads, the techniques described herein may enable a clinician and/or a medical device to select electrodes suited for delivery of efficacious electrical stimulation therapy or sensing of biosignals from the patient, thereby increasing the efficacy of electrical stimulation therapy and/or decreasing the risk of side effects of the electrical stimulation therapy. Further, the techniques of the disclosure may enable the identification of anatomical structures within tissues of the patient, such as soft tissue structures within the patient.

Figure 2:
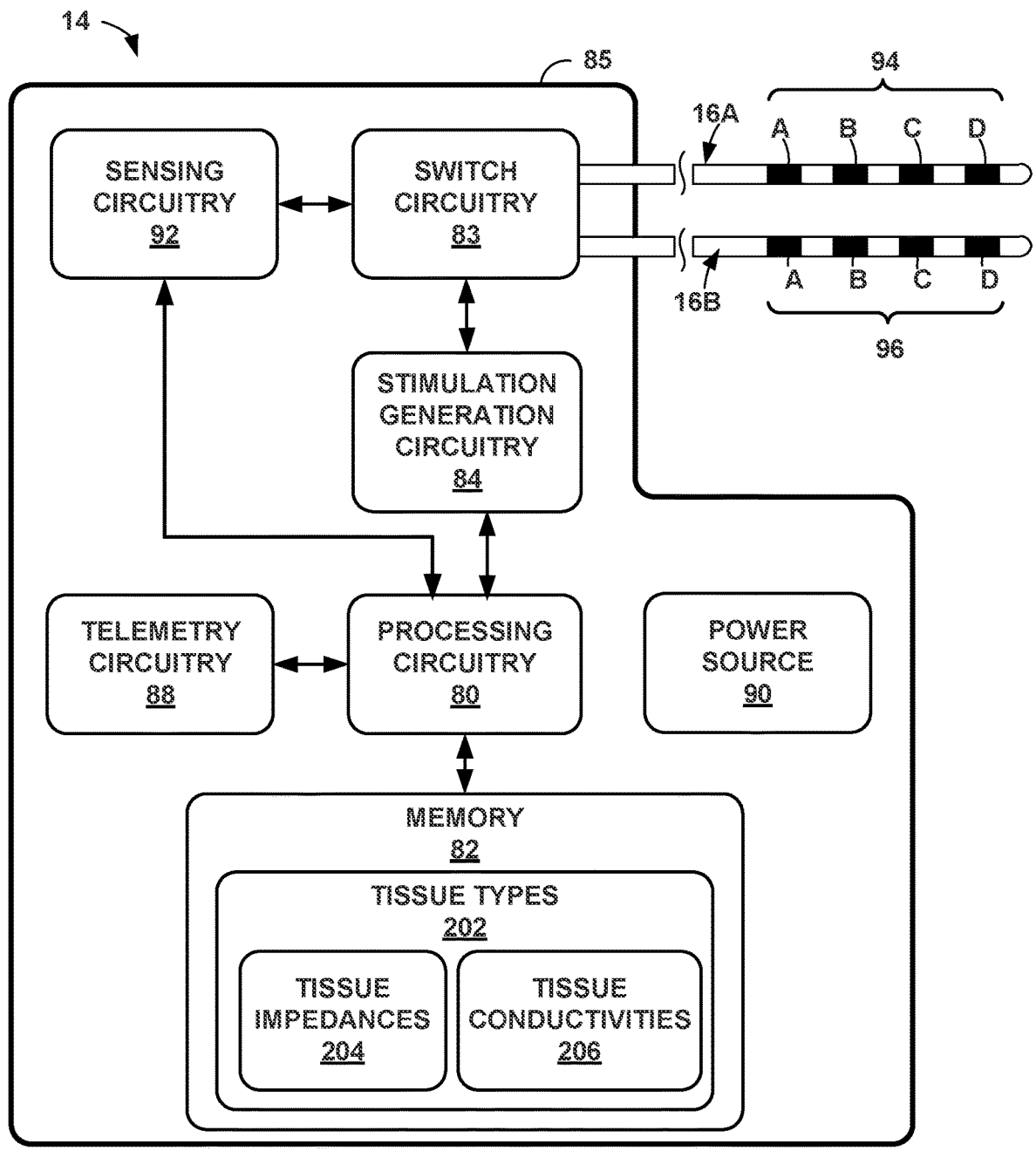
FIG. 2 is a functional block diagram illustrating an example of the IMD of FIG. 1 in further detail.

FIG. 2 is a functional block diagram illustrating various components of an IMD 14. In the example of FIG. 2, IMD 14 includes a housing 85, processing circuitry 80, memory 82, switch circuitry 83, stimulation generation circuitry 84, telemetry circuit 88, power source 90, and sensing circuitry 92. The stimulation generation circuitry 84 may form a therapy delivery module. Processing circuitry 83 may control switch circuitry 83 which switches signals to and/or from leads 16 to sensing circuitry 92 and/or stimulation generation circuitry 84. Memory 82 may store instructions for execution by processing circuitry 80, stimulation therapy data, evoked compound action potential (ECAP) characteristic values, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions including instructions for ECAP analysis, posture state information, therapy adjustment information, prior detected ECAP signals and/or characteristic values of ECAPs, program histories, and any other pertinent data or instructions.

Processing circuitry 80 controls stimulation generation circuitry 84 to deliver electrical stimulation via electrode combinations formed by electrodes in one or more electrode arrays. For example, stimulation generation circuitry 84 may deliver electrical stimulation therapy via electrodes (e.g., electrodes 94A-94D and 96A-86D of respective leads 16A and 16B) on one or more leads 16, e.g., as stimulation pulses or continuous waveforms. Components described as processing circuitry within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generation circuitry 84 may include stimulation generation circuitry to generate stimulation or a stimulus (in the form of pulses or waveforms) and switching circuitry to switch the stimulation across different electrode combinations, e.g., in response to control by processing circuitry 80. In particular, processing circuitry 80 may control the switching circuitry on a selective basis to cause stimulation generation circuitry 84 to deliver electrical stimulation to selected electrode combinations and to shift the electrical stimulation to different electrode combinations in a first direction or a second direction when the therapy must be delivered to a different location within patient 12. In other examples, stimulation generation circuitry 84 may include multiple current sources and sinks to drive more than one electrode combination at one time. For example, each electrode may have its own current source and current sink, which can be selectively activated so that the electrode can source or sink controlled amounts of current. An electrode configuration, e.g., electrode combination and associated electrode polarities, may be represented by a data stored in a memory location, e.g., in memory 82, of IMD 14. Processing circuitry 80 may access the memory location to determine the electrode combination and control stimulation generation circuitry 84 to deliver electrical stimulation via the indicated electrode combination. To adjust electrode combinations, amplitudes, pulse rates, or pulse widths, processing circuitry 80 may command stimulation generation circuitry 84 to make the appropriate changes to therapy according to instructions within memory 82 and rewrite the memory location to indicate the changed therapy. In other examples, rather than rewriting a single memory location, processing circuitry 80 may make use of two or more memory locations.

When activating stimulation, processing circuitry 80 may access not only the memory location specifying the electrode combination but also other memory locations specifying various stimulation parameters such as voltage or current amplitude, pulse width and pulse rate. Stimulation generation circuitry 84, e.g., under control of processing circuitry 80, then makes use of the electrode combination and parameters in formulating and delivering the electrical stimulation to patient 12.

Processing circuitry 80 accesses stimulation parameters in memory 82, e.g., as programs and groups of programs. Upon selection of a particular program group, processing circuitry 80 may control stimulation generation circuitry 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processing circuitry 80 also may control telemetry circuit 88 to send and receive information to and from external programmer 20. For example, telemetry circuit 88 may send information to and receive information from programmer 20.

In addition, IMB 14 may store patient 12 input regarding perceived physiological conditions (e.g., symptoms) not detectable by any implemented sensors. For example, patient 12 may provide input to programmer 20 that indicates where the patient perceives any symptoms and characteristics of that particular type of symptom. processing circuitry 80 may associate this physiological condition information with the currently detected posture state, the stimulation parameters, and/or a time stamp to provide a complete therapy picture to the patient or clinician at a later time. Such information may be stored in memory 82 of IMD 14, the memory of programmer 20, and/or the memory of some other device.

Wireless telemetry in IMD 14 with external programmer 20, e.g., a patient programmer or a clinician programmer, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Sensing circuitry 92 may be configured to detect signals from a tissue of the patient. In other examples, sensing circuitry 92 may be located on lead 16, and may include for, example, one or more of the electrodes in leads 16 in combination with suitable amplification, filtering and/or signal processing circuitry. In some examples, sensing circuitry 92 may include an additional electrode on housing 85 of IMD 14. In some examples, Sensing circuitry 92 may be carried by an additional sensor lead positioned somewhere within patient 12, provided as an independent implantable sensor, or even worn on patient 12.

Processing circuitry 80 may be configured to control stimulation generation circuitry 84 to deliver an electrical stimulus via a first electrode 94. Processing circuitry 80 controls sensing circuitry 92 to sense, via each of the other electrodes 94, respective electrical signals indicative of the electrical stimulus. In some examples, the electrical signals are indicative of the voltage amplitude at each of the other electrodes 94. For example, processing circuitry 84 controls stimulation generation circuitry 84 to deliver, via electrode 94A, an electrical stimulus defined by a first voltage amplitude. Processing circuitry 84 senses, via sensing circuitry 92 and at each of electrodes 94B, 94C, 94D, and 96A-96D, respective electrical signals indicative of the electrical stimulus, e.g., a voltage amplitude at each of electrodes 94B, 94C, 94D, and 96A-96D resulting from delivery of the electrical stimulus at electrode 94A.

Processing circuitry 84 determines, based on the respective sensed electrical signals indicative of the electrical stimulus, a distance of electrode 94A to each of the other electrodes 94, 96. For example, processing circuitry 84 determines a difference between the voltage delivered at electrode 94A and a sensed voltage at, e.g., electrode 96A. In some examples, processing circuitry 84 uses a tissue conductivity between electrodes 94A, 96A (calculated as described below) to convert the difference between the voltage amplitude of the electrical stimulus delivered at electrode 94A and the sensed voltage amplitude at electrode 96A (e.g., the voltage drop between electrodes 94A and 96A) into a spatial relationship. Processing circuitry 84 may repeat the foregoing process for each electrode of disposed on leads 16 to determine, e.g., a spatial relationship of each electrode of disposed on leads 16 to each other lead disposed on leads 16 to determine, e.g., a distance of each electrode 94, 96 to each other electrode 94, 96. For example, by knowing the voltage amplitude of an electrical stimulus delivered at electrode 94A, the area of electrodes 94 on lead 16A and electrodes 96 on lead 16B, a tissue conductivity of a tissue interposed between electrode 94A and electrode 96A, a tissue impedance of the tissue interposed between electrode 94A and electrode 96A, and a voltage amplitude sensed at electrode 96A, processing circuitry 84 may apply geometric and trigonometric operations to determine a spatial relationship between electrodes 94A and 96A, such as a scalar distance, a vector, or an orientation, etc. In some examples where only the distance between electrode 94A and electrode 96A is desired, the voltage amplitude sensed at, e.g., electrode 94B and/or the spacing of electrodes on lead 16A may not be needed.

Processing circuitry 84 uses the calculated distances of each electrode 94, 96 to each other electrode 94, 96 to, e.g., select one or more electrodes 94, 96 for subsequent delivery of electrical stimulation or for sensing a biosignal of patient 12. In some examples, processing circuitry 84 uses the calculated distances of each electrode 94, 96 to each other electrode 94, 96 to adjust one or more electrical stimulation parameters for subsequent delivery of electrical stimulation and delivers electrical stimulation in accordance with the adjusted one or more parameters. For example, processing circuitry 84 may use the calculated distances of each electrode 94, 96 to each other electrode 94, 96 to increase a value of an electrical stimulation parameter (e.g., a current or voltage amplitude) for electrodes 94, 96 further from a target tissue of the patient and decrease a value of the electrical stimulation parameter (e.g., a current or voltage amplitude) for electrodes 94, 96 closer to the target tissue of the patient. Further, processing circuitry 84 may adjust the value of the electrical stimulation parameter of each other electrode 94, 96 in proportion to a distance of each other electrode 94, 96 to the target tissue of the patient with respect to a distance of the first electrode 94A to the target tissue.

In some examples, processing circuitry 84 outputs, via telemetry circuitry 88, the calculated distances of each electrode 94, 96 to each other electrode 94, 96 to external programmer 20. As described in more detail below, external programmer 20 may generate a 2-dimensional or 3-dimensional (3D) representation of the calculated distances of each electrode 94, 96 to each other electrode 94, 96 for display to a user.

In some examples, processing circuitry 80 determines an impedance between electrodes 94, 96. For example, processing circuitry 80 may determine an impedance between various combinations or pairs of electrodes 94, 96 and/or housing 85 of IMD 14. For example, processing circuitry 80 may control stimulation generation circuitry 84 to deliver a stimulus (e.g., at a known voltage and current) via a first electrode of electrodes 94 and sense, via sensing circuitry 92, a resultant signal via a second electrode of electrodes 94. By delivering a stimulus with a known voltage and/or current and determining a value of the signal sensed by another electrode, processing circuitry 80 may compute the impedance of a material (e.g., a tissue) between a pair of electrodes in accordance with the following equation:

$$\text{Impedance } Z = \frac{\text{Voltage } V}{\text{Current } I},$$

$$\text{Conductance } G = \frac{1}{\text{Impedance } Z}$$

Processing circuitry 80 can then determine, based on the sensed impedances, a type of a tissue interposed between each of the pairs of electrodes 94, 96 and/or housing 85 of IMD 14. For example, memory 82 may store, e.g., as a look-up table, a plurality of tissue types 202, a corresponding tissue impedance 204 for each of the plurality of tissue types 202, and a corresponding tissue conductivity 206 for each of the plurality of tissue types 202. For example, tissue types 202 may include a nerve tissue, a bone tissue, a connective tissue, or an adipose tissue, and memory 82 may store, e.g., a tissue impedance 204 and a tissue conductivity 206 for each of the nerve tissue, the bone tissue, the connective tissue, or the adipose tissue.

Processing circuitry 80 compares, for each pair of electrodes 94, 96 and/or housing 85 of IMD 14, a value of the sensed impedance to a value of the tissue impedance 204 of each tissue type 202. In response to determining that the value of the sensed impedance of the pair of electrodes 94, 96 and/or housing 85 of IMD 14 matches a value of a tissue impedance 204, processing circuitry 80 determines that the tissue interposed between the pair of electrodes 94, 96 and/or housing 85 of IMD 14 is a tissue type corresponding to the matching tissue type 202. Thus, in this manner, processing circuitry 84 determines, based on the sensed impedances, a type of a tissue interposed between each of the pairs of electrodes 94, 96 and/or housing 85 of IMD 14. Further, processing circuitry 84 determines, based on the type of the tissue, a tissue conductivity of the tissue interposed between each of the pairs of electrodes disposed on leads 16. For example, processing circuitry 84 retrieves, based on the tissue type 202, a corresponding tissue conductivity 206. Processing circuitry 84 uses the tissue conductivity 206 between two electrodes 94, 96 to convert a difference between a voltage amplitude of the electrical stimulus delivered at a first electrode 94, 96 and the sensed voltage amplitude at a second electrode 94, 96 into the spatial relationship between the pair of electrodes 94, 96.

The conductivity for different tissues between electrodes can be determined and used as described herein to identify the spacing of electrodes. For example, the cell constant K is a ratio of a distance d between a pair of electrodes 94, 96 to an effective area a of the electrodes 94, 96, as defined below:

$$K = \frac{d}{a}$$

Processing circuitry 80 may compute a conductivity σ using the conductance G and the cell constant K calculated above, wherein conductivity σ=conductance G×cell constant K. From the previous equations the following relationship is defined:

$$\text{conductivity } \sigma = \left(\frac{1}{\text{Impedance } Z}\right)\left(\frac{\text{Distance } d \text{ between a pair of electrodes}}{\text{Effective area } a \text{ of the electrodes}}\right)$$

Using the known value of the electrode area a, a value of impedance I measured by processing circuitry 80, and a value of conductivity σ retrieved from memory 82, the above equation can be rearranged to enable processing circuitry 80 to solve for an unknown value of distance d between a pair of electrodes 94, 96:

distance d=(conductivity σ)(effective area a of the electrodes)(Impedance I)

The above relationship may also be stated in terms of voltage and current:

$$\sigma = G \times K = \left(\frac{1}{Z}\right)\left(\frac{d}{a}\right) = \left(\frac{I}{V}\right)\left(\frac{d}{a}\right)$$

$$d = \frac{\sigma \times a \times V}{I}$$

In some examples, IMD 14 may include additional circuitry (not depicted in FIG. 2) for measuring conductivity σ of the tissue interposed between the pair of electrodes 94, 96. In some examples, if distance d between a pair of electrodes 94, 96 (such as, for example, electrodes 94A and 94B affixed at a known separation distance on lead 16A), then processing circuitry 80 may instead calculate conductivity of the tissue interposed between the electrodes 94, 96.

Figure 3:
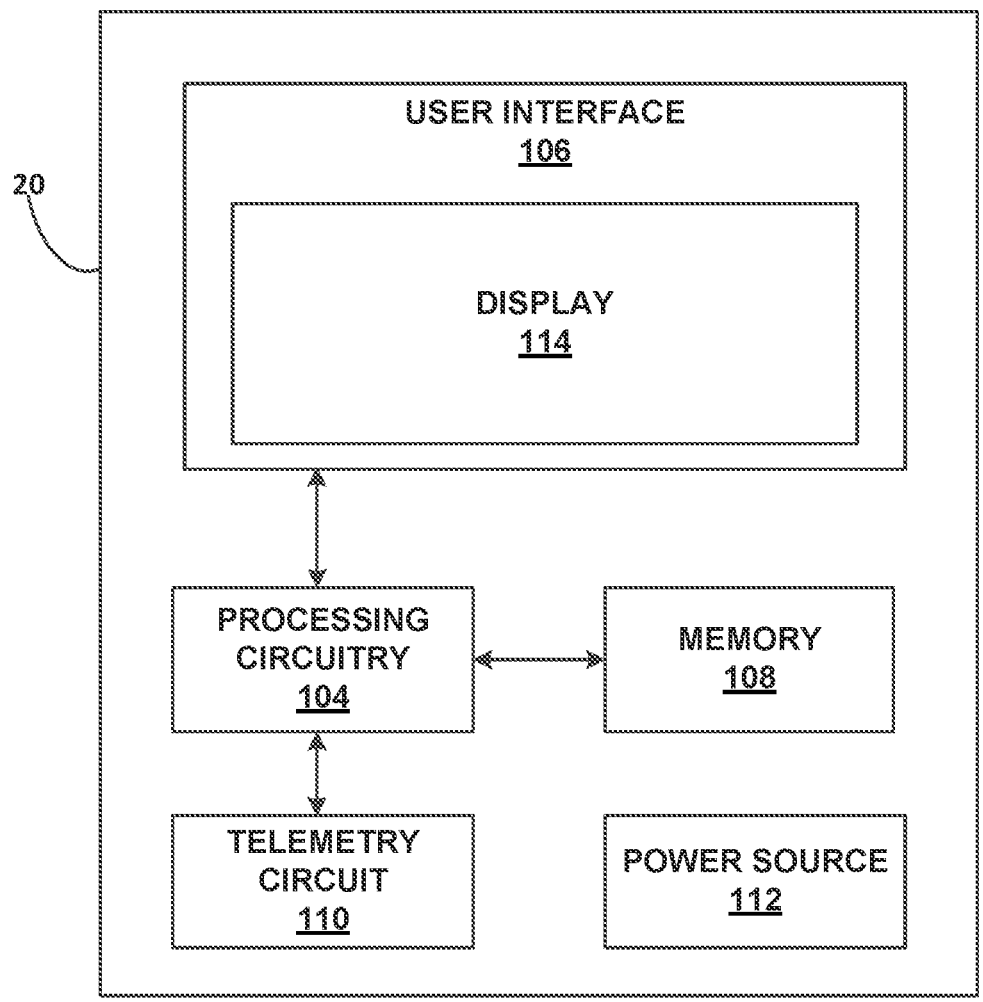
FIG. 3 is a functional block diagram illustrating an example of the external programmer of FIG. 1 in further detail.

FIG. 3 is a functional block diagram illustrating various components of an external programmer 20 for IMD 14. As shown in FIG. 3, external programmer 20 is an external device that includes processing circuitry 104, memory 108, telemetry circuit 110, user interface 106, and power source 112. External programmer 20 may be embodied as a patient programmer or a clinician programmer.

A clinician or patient 12 interacts with user interface 106 in order to manually change the stimulation parameters of a program, change programs within a group, turn electrical stimulation ON or OFF, view therapy information, view patient state information, view a posture state indication, or otherwise communicate with IMD 14. Processing circuitry 104 controls user interface 106, retrieves data from memory 108 and stores data within memory 108. Processing circuitry 104 also controls the transmission of data through telemetry circuit 110 to IMDs 14 or 26. Memory 108 includes operation instructions for processing circuitry 104 and data related to patient 12 therapy.

User interface 106 may comprise one or more input devices and one or more output devices. The input devices of user interface 106 may include a communication device such as a keyboard, pointing device, voice responsive system, video camera, biometric detection/response system, button, sensor, control pad, microphone, presence-sensitive screen, or any other type of device for detecting input from the user.

The output devices of user interface 106 may include a communication unit such as a display, sound card, video graphics adapter card, speaker, presence-sensitive screen, one or more USB interfaces, video and/or audio output interfaces, or any other type of device capable of generating tactile, audio, video, or other output. The output devices of user interface 106 may include a display device 114, which may function as an output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In other examples, the output devices of user interface 106 may produce an output to a user in another fashion, such as via a sound card, video graphics adapter card, speaker, presence-sensitive screen, one or more USB interfaces, video and/or audio output interfaces, or any other type of device capable of generating tactile, audio, video, or other output. In some examples, the output devices of user interface 106 may include a presence-sensitive display that may serve as a user interface device that operates both as one or more input devices and one or more output devices.

Telemetry circuit 110 allows the transfer of data to and from IMB 14. Telemetry circuit 110 may communicate automatically with IMD 14 in real-time, at a scheduled time, or when the telemetry circuit detects the proximity of the stimulator. User interface 106 may then update displayed information accordingly. Alternatively, telemetry circuit 110 may communicate with IMB 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMB 14. In other cases, the programmer may be integrated with a recharging functionality in the combined programming/recharging device. The techniques described herein may be communicated between IMD 14 via any type of external device capable of communication with IMD 14.

In some examples, processing circuitry 104 receives, via telemetry circuit 110, measurements sensed by IMD 14 and uses such information to determines spatial relationships between electrodes 94, 96 disposed on leads 16 in the manner described above. Further, processing circuitry 104 may select, based on the spatial relationships of the first electrode to each of the other electrodes, one or more electrodes 94, 96 and control IMB 14 to deliver electrical stimulation therapy or sense a biosignal of patient 12 via the selected one or more electrodes 94, 96.

In some examples, processing circuitry 104 generates a representation of the plurality of electrodes 94, 96 disposed on leads 16 that depicts the spatial relationships of each electrode 94, 96 to each of the other electrodes 94, 96. In some examples, the representation of electrodes 94, 96 depicts a 2D or 3D spatial relationship of lead 16A to 16B and/or a 3D spatial relationship of electrodes 94, 96 to one another. Such a representation may depict, e.g., a distance of each electrode 94, 96 to each of the other electrodes 94, 96. In other examples, processing circuitry 104 may control user interface 106 to present numerical distances alone, or in addition to graphical depiction of the spatial relationships between electrodes.

In some examples, processing circuitry 104 generates a representation that comprises a 3D model the plurality of electrodes 94, 96 disposed on leads 16. Using the calculated distances of each electrode 94, 96 to each of the other electrodes 94, 96, processing circuitry 104 may adjust, warp, stretch, or skew the shape or position of an normally straight lead 16A, lead 16B, and each electrode 94, 96 disposed on leads 16 to more accurately depict a true location of electrodes 94, 96 and leads 16 within the body of patient 12. In this manner, user interface 106 may be controlled by processing circuitry 104 to present leads in the shape as implanted within the patient. Processing circuitry 104 displays the representation of the plurality of electrodes 94, 96 disposed on leads 16 to a user via display 114.

Figure 4:
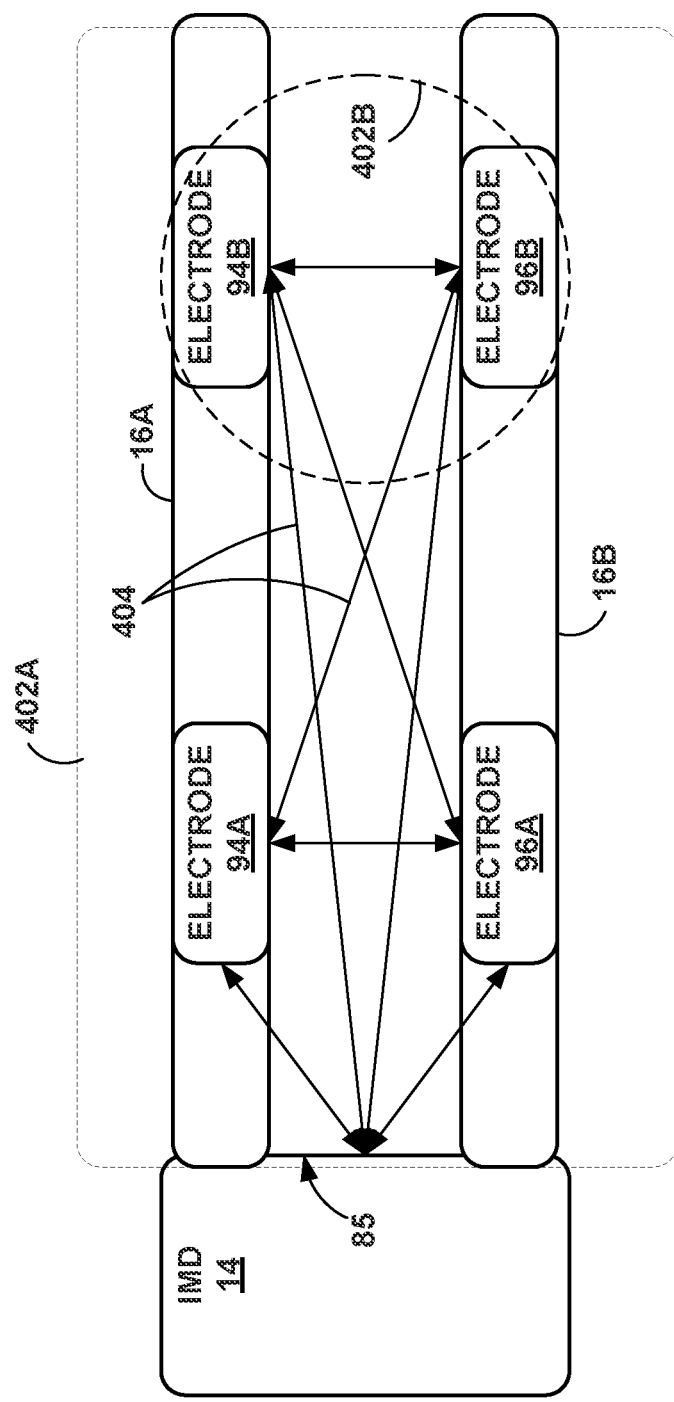
FIG. 4 is a conceptual illustration of example electrodes in accordance with the techniques of the disclosure.

FIG. 4 is a conceptual illustration of example electrodes in accordance with the techniques of the disclosure. For convenience, FIG. 4 is described with respect to FIGS. 1 and 2. In the example of FIG. 4, IMB 14 and leads 16 are implanted within patient 14. Lead 16A comprises electrodes 94A and 94B and lead 16B comprises electrodes 96A and 96B. Electrodes 94A and 96A are implanted within tissue 402A that comprises a first tissue type (e.g., nerve tissue). Electrodes 94B and 96B are implanted within tissue 402B that comprises a second tissue type (e.g., bone tissue).

IMD 14 determines an impedance between electrodes 94, 96. For example, IMD 14 senses an impedance between various combinations or pairs of electrodes 94, 96 and/or housing 85 of IMD 14. For example, IMB 14 delivers a stimulus (e.g., at a known voltage and current) via electrode 94A and senses a resulting first signal via electrode 96A. As another example, IMB 14 delivers a stimulus via electrode 94B and senses a resulting second signal via electrode 96B. In some examples, IMD 14 delivers a stimulus via electrode 94A and senses a resulting third signal via housing 85. By delivering a stimulus with a known voltage and/or current and determining a value of the signal sensed by another electrode, IMD 14 may compute the impedance between a pair of electrodes. In the foregoing examples, IMD 14 computes a first impedance between electrodes 94A and 96A, a second impedance between electrodes 94B and 96B, and a third impedance between electrode 94A and housing 85.

IMD 14 determines, based on the sensed impedances, a type of a tissue interposed between each pair of electrodes 94, 96 and/or housing 85 of IMD 14. For example, IMB 14 may use the first, second, and third sensed impedances to look up tissue impedances 204 and corresponding tissue types 202 stored in memory 82. For example, IMD 14 determines that the first impedance between electrodes 94A and 96A and the third impedance between electrode 94A and housing 85 correspond to a tissue impedance of nerve tissue, and so determines that tissue 402A comprises nerve tissue. Similarly, IMB 14 may determine that the second impedance between electrodes 94B and 96B corresponds to a tissue impedance of bone tissue, and so determines that tissue 402B comprises bone tissue. IMD 14 retrieves from memory 82, a tissue conductivity for nerve tissue (e.g., tissue 402A) and bone tissue (e.g., tissue 402B).

IMD 14 may be configured to deliver an electrical stimulus via a first electrode 94, 96 and sense an electrical signal indicative of the electrical stimulus via a second electrode 94, 96. IMD 14 may use a magnitude of the electrical stimulus, the sensed electrical signal indicative of the electrical stimulus, and a tissue conductivity interposed between the first and second electrodes 94, 96 to determine a distance 404 between the first and second electrodes 94, 96.

For example, IMB 14 senses between electrode 94A and electrode 96A, a value of impedance of 2,500 Ohms. By using a tissue conductivity value of 0.265 Siemens per meter for nerve tissue for tissue 402A and the area of electrodes 94A and 96A of approximately 12 square millimeters, IMD 14 determines that electrodes 94A and 96A are 7.95 millimeters from one another. These values may be different for other electrode materials, sizes, or other variations, as indicated in another example below.

As another example, IMB 14 senses between electrode 94B and electrode 96B, a value of impedance of 100,000 Ohms. By using a tissue conductivity value of 3.5e−3 Siemens per meter for bone tissue for tissue 402B and area of electrodes 94B and 96B of approximately 12 square millimeters, IMD 14 determines that electrodes 94B and 96B are 4.2 millimeters from one another.

Processing circuitry 84 may repeat the foregoing process for each electrode of disposed on leads 16 to determine, e.g., a distance 404 of each electrode 94A, 94B, 96A, 96B to each other electrode 94A, 94B, 96A, 96B and housing 85. In some examples, processing circuitry 84 may apply a scaling factor to sensed voltages at each of electrodes 94, 96 to determine the distance between each of electrodes 94, 96. Additional description of the use of such a scaling factor is described below with respect to FIG. 8.

Figure 5:
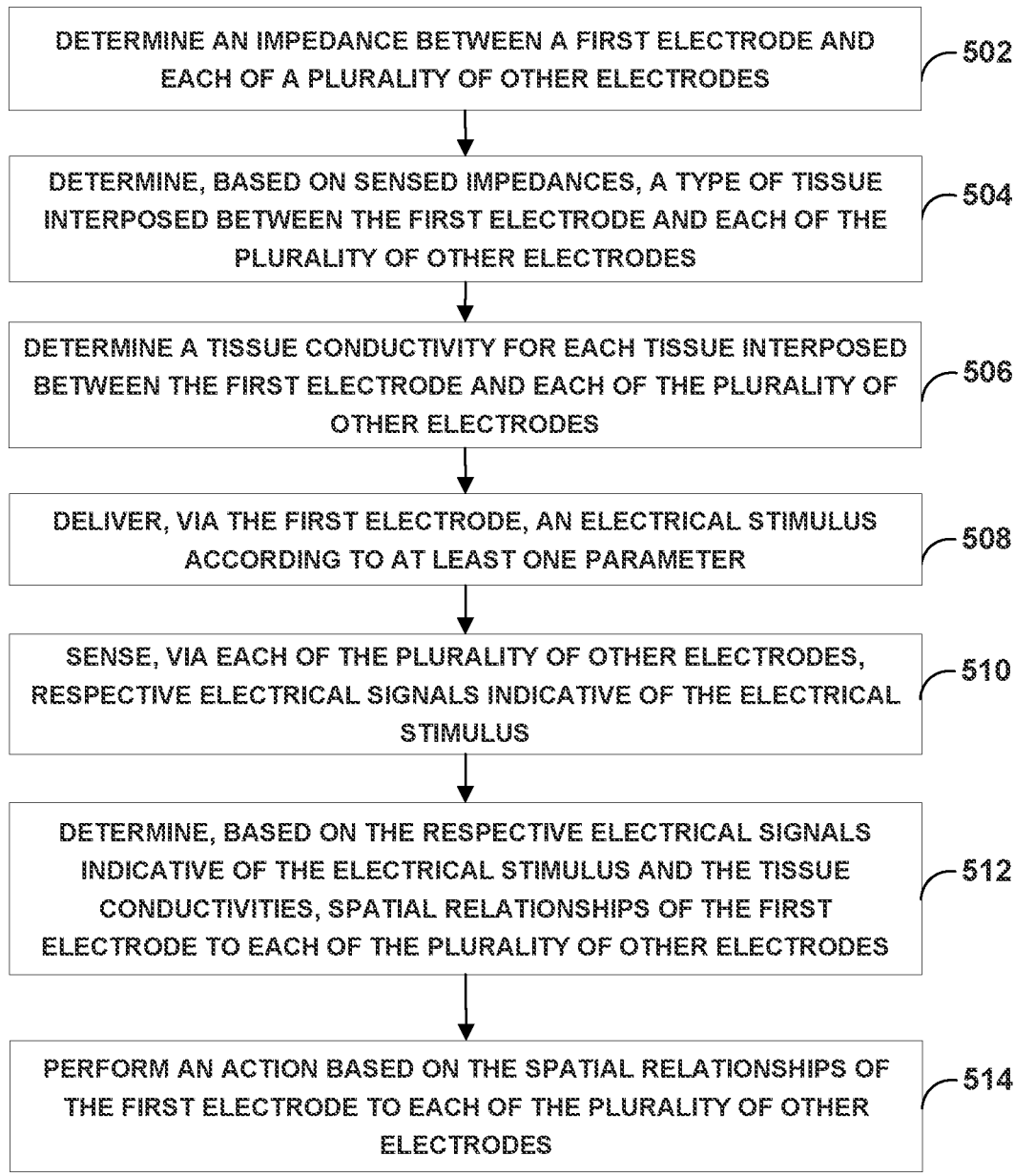
FIG. 5 is a flowchart illustrating an operation in accordance with the techniques of the disclosure.

FIG. 5 is a flowchart illustrating an operation in accordance with the techniques of the disclosure. For convenience, FIG. 5 is described with respect to IMB 14 of FIGS. 1 and 2. However, portions of the operation of FIG. 5 may be performed by other devices, such as external programmer 20 of FIGS. 1 and 3.

In the example of FIG. 5, IMB 14 determines an impedance between electrode 94A and a plurality of other electrodes 94, 96 and housing 85 (502). For example, IMB 14 delivers a stimulus via electrode 94A and senses a resulting signal via each of electrodes 94B-94D, 96A-96D, and housing 85. By delivering a stimulus with a known voltage and/or current and determining a value of the signal sensed by another electrode, IMD 14 determines the impedance between electrode 94A and each of the plurality of other electrodes 94, 96 and housing 85.

IMD 14 can then determine, based on the sensed impedances, a type of tissue interposed between electrode 94A and each of the plurality of other electrodes 94, 96 and housing 85 (504). For example, memory 82 of IMD 14 may store, e.g., as a look-up table, a plurality of tissue types 202, a corresponding tissue impedance 204 for each of the plurality of tissue types 202, and a corresponding tissue conductivity 206 for each of the plurality of tissue types 202. For example, tissue types 202 may include a nerve tissue, a bone tissue, a connective tissue, or an adipose tissue, and memory 82 may store, e.g., a tissue impedance 204 and a tissue conductivity 206 for each of the nerve tissue, the bone tissue, the connective tissue, or the adipose tissue.

IMD 14 may then compare, for each pair comprising electrode 94A and one of electrodes 94, 96 and housing 85, a value of the sensed impedance to a value of the tissue impedance 204 of each tissue type 202. In response to determining that the value of the sensed impedance of the pair matches a value of a tissue impedance 204, IMB 14 determines that the tissue interposed between the pair is a tissue type corresponding to the matching tissue type 202 stored in memory 82. Thus, in this manner, IMD 14 determines, based on the sensed impedances, a type of a tissue interposed between electrode 94A and each of the plurality of other electrodes 94, 96 and housing 85. Further, IMD 14 determines, based on the type of the tissue, a tissue conductivity of the tissue interposed between electrode 94A and each of the plurality of other electrodes 94, 96 and housing 85 (506). For example, processing circuitry 84 retrieves, based on the tissue type 202, a corresponding tissue conductivity 206. In other examples, IMD 14 may obtain an estimated or assumed tissue conductivity to be used in the process to follow instead of measuring actual conductivity as described in steps 502, 504, and 506.

IMD 14 may be configured to deliver an electrical stimulus via electrode 94A according to at least one parameter (508). Further, IMB 14 senses, via each of the plurality of other electrodes 94, 96 and housing 85, respective electrical signals indicative of the electrical stimulus (510). In some examples, the parameter is a voltage amplitude. For example, IMD 14 delivers, via electrode 94A, an electrical stimulus according to a first voltage amplitude. IMD 14 senses, at each of the plurality of other electrodes 94, 96 and housing 85, respective electrical signals indicative of the electrical stimulus, e.g., a value of a voltage amplitude resulting from delivery of the electrical stimulus at electrode 94A.

IMD 14 determines, based on the respective electrical signals indicative of the electrical stimulus and the tissue conductivity 206 of the tissues interposed between electrode 94A and each of the plurality of other electrodes 94, 96 and housing 85, a spatial relationship of electrode 94A to each other electrode (512). For example, IMB 14 determines a difference between a value of the voltage amplitude of the electrical stimulus delivered at electrode 94A and a value of a sensed voltage amplitude at, e.g., electrode 96A. IMD 14 uses a tissue conductivity of the tissue interposed between electrodes 94A, 96A to convert the difference between the voltage amplitude of the electrical stimulus delivered at electrode 94A and the sensed value of the voltage amplitude at electrode 96A (e.g., the voltage drop between electrodes 94A and 96A) into a spatial relationship, such as a distance. IMD 14 may repeat the foregoing process between electrode 94A and each of the plurality of other electrodes 94, 96 and housing 85 to determine, e.g., a spatial relationship of electrode 94A to electrode 94A and each of the plurality of other electrodes 94, 96 and housing 85.

IMD 14 and/or external programmer 20 performs an action based on the calculated spatial relationships of electrode 94A to electrode 94A and each of the plurality of other electrodes 94, 96 and housing 85 (514). For example, IMB 14 uses the calculated spatial relationships between electrode 94A and each of the plurality of other electrodes 94, 96 and housing 85 to, e.g., select one or more electrodes 94, 96 for subsequent delivery of electrical stimulation and deliver electrical stimulation via the selected one or more electrodes 94, 96. As another example, IMB 14 uses the calculated spatial relationships between electrode 94A and each of the plurality of other electrodes 94, 96 and housing 85 to, e.g., adjust one or more electrical stimulation parameters for subsequent delivery of electrical stimulation and deliver electrical stimulation in accordance with the adjusted one or more parameters. As another example, IMB 14 uses the calculated spatial relationships between electrode 94A and each of the plurality of other electrodes 94, 96 and housing 85 to, e.g., select one or more electrodes 94, 96 for subsequent sensing of a biosignal of patient 12 and senses the biosignal of patient 12. As another example, IMD 14 outputs, to external programmer 20, the calculated spatial relationships of each electrode 94, 96 to each other electrode 94, 96 to external programmer 20. External programmer 20 may generate a representation of the calculated spatial relationships of each electrode 94, 96 to each other electrode 94, 96 in 2 or 3 dimensions and output the representation of the spatial relationships for display to a user. In another example, IMD 14 may scale user inputs for stimulation parameter values according to the spatial relationships between electrodes. The user may be expecting that the leads are parallel to each other and select amplitudes or pulse widths, for example, accordingly. Instead of showing the user how the electrode distances vary, IMD 14 may instead scale the user or system selected parameter values to account for the differences in distances between electrodes. For instance, IMD 14 may reduce current amplitude values for electrodes closer together than expected and increase current amplitude values for electrodes further apart than expected. The external programmer (e.g., programmer 20) may present an indication that such corrections to parameter values are being made.

Figure 6:
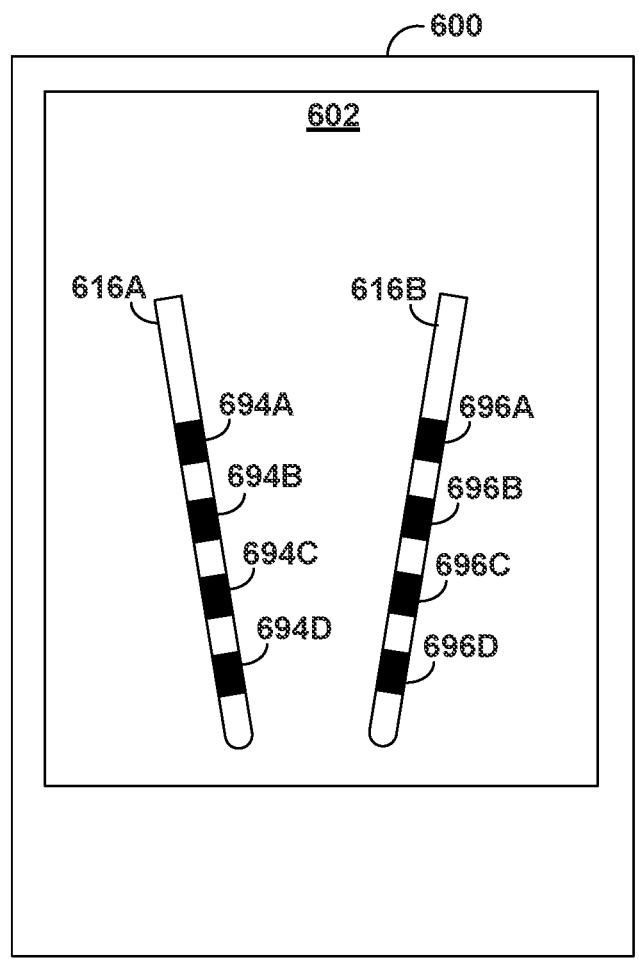
FIG. 6 is an illustration depicting an example user interface of the external programmer of FIG. 3.

FIG. 6 is an illustration depicting an example user interface 602 of external programmer 20 of FIG. 3. In some examples, user interface 600 is an example of user interface 106 of external programmer 600 of FIG. 3. User interface 600 may be used to display spatial relationships between electrodes 94, 96 of leads 16 as described above. FIG. 6 depicts display window 602 of user interface 600, which is displaying example lead icons 616A and 616B (collectively, "lead icons 616"), which may correspond to leads 16A and 16B, respectively, of IMD 14.

In the example of FIG. 6, lead icon 616A includes four electrode icons 696A-696D (collectively, "electrode icons 694") and lead icon 616B includes four electrode icons 696A-696D (collectively, "electrode icons 696"). Electrode icons 694 may correspond to electrodes 94 of IMD 14 and electrode icons 696 may correspond to electrodes 96 of IMD 14.

Lead icons 616 may have more, or fewer, electrode icons 694, 696, depending on the particular lead configuration in use, and other numbers of lead icons 616 may be displayed on screen 602. For ease of illustration, only four electrode icons 694, 696 (or a portion of four electrodes) are depicted on each of lead icons 616. In addition, window 602 may depict stimulation zones, electrical field zones, activation zones, etc. (not shown), that correspond to the stimulation deliverable by various electrode combinations. In addition, or alternatively, user interface 600 may present lead icons 616 with respect to one or more anatomical structures of the patient, such as a spinal cord, vertebrae, epidural space, skin, etc. Any of the devices described herein may utilize the calculated impedances, voltages, or other characteristics of sensed electrical signals to determine distances from the electrodes to anatomical regions and place each lead icons 616 at an appropriate distance from such structures.

As described above, external programmer 20 may be configured to generate a representation that depicts the spatial relationships of each electrode 94, 96 to each of the other electrodes 94, 96, via corresponding electrode icons 694, 696. In some examples, lead icons 616 depict a 2D or 3D spatial relationship of lead 16A to 16B and/or electrode icons 694, 696 depict a 2D or 3D spatial relationship of each of electrodes 94, 96 to each other electrode 94, 96. For example, electrode icons 694, 696 depict a distance of each of electrodes 94, 96 to each other electrode 94, 96.

In some examples, lead icons 616 and electrode icons 694, 696 comprise a 3D model of leads 16 and electrodes 94, 96 of IMD 20. External programmer 20 uses the determined spatial relationships of each of electrodes 94, 96 to each other electrode 94, 96 to adjust, warp, stretch, or skew the shape or position of lead icons 616 and electrode icons 694, 696 to more accurately depict a true location of electrodes 94, 96 and leads 16 within the body of patient 12. For example, as depicted in FIG. 6, external programmer 20 adjusts lead icon 616A and lead icon 616B relative to lead icon 616A to more accurately depict a true location of electrodes 94, 96 and leads 16 within the body of patient 12.

Figure 7B:
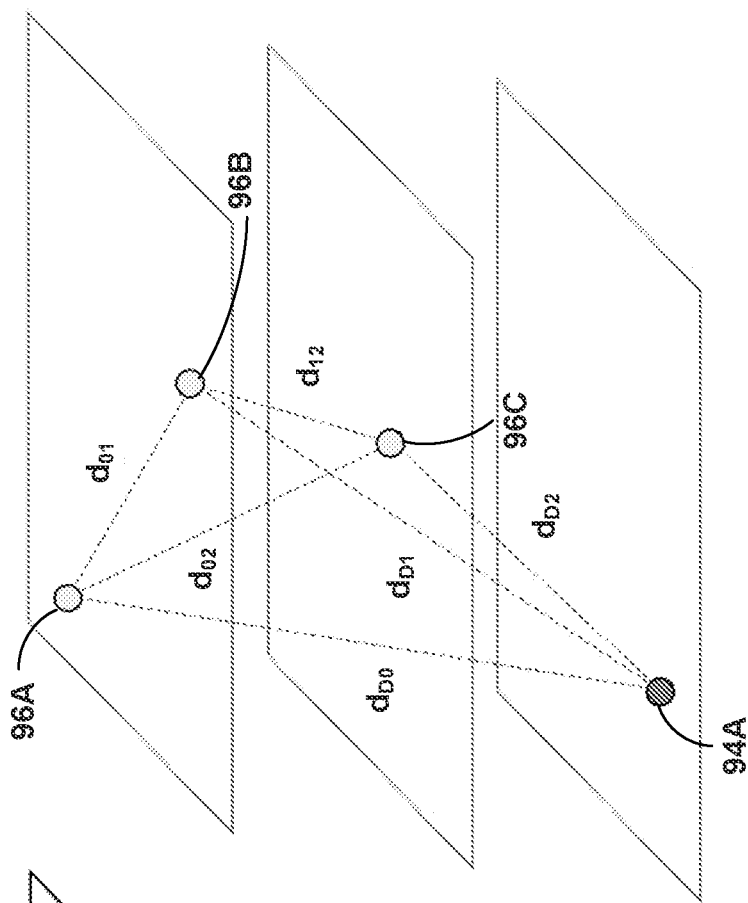
FIGS. 7A-7B are conceptual illustrations of example electrodes in accordance with the techniques of the disclosure.
Figure 7A:
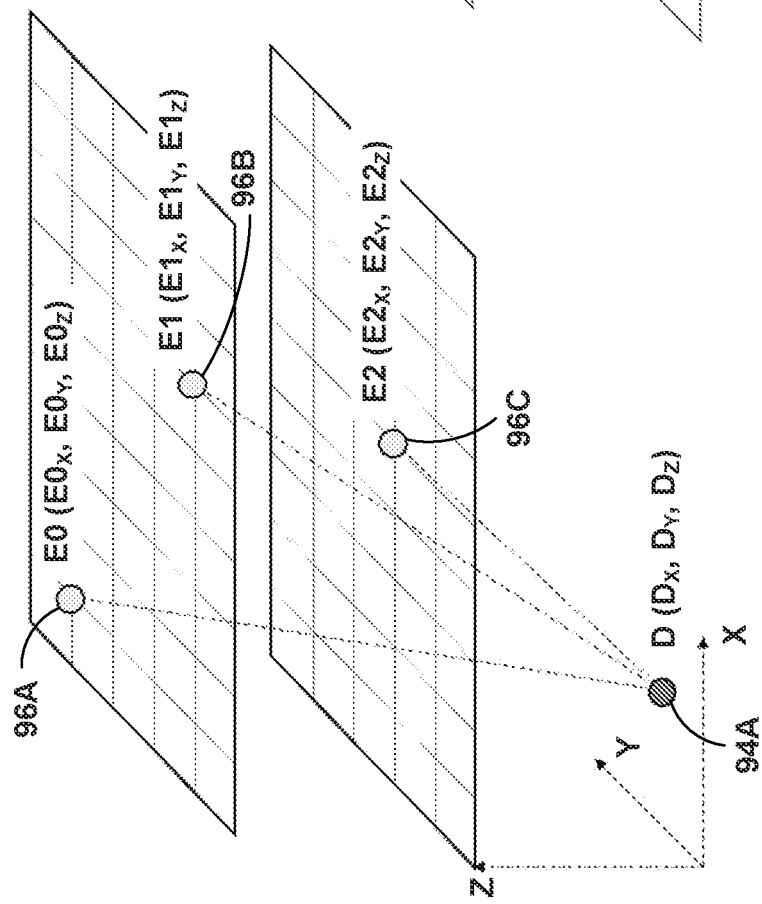

FIGS. 7A-7B are conceptual illustrations of example electrodes 94, 96 and distances between each electrode in accordance with the techniques of the disclosure. For convenience, FIGS. 7A and 7B are described with respect to IMB 14 of FIG. 2. As depicted in the example of FIG. 7A, electrode 94A is located at a position D comprising planar coordinates ($D_X$, $D_Y$, $D_Z$), electrode 96A is located at a position E0 comprising planar coordinates ($E0_X$, $E0_Y$, $E0_Z$), electrode 96B is located at a position E1 comprising planar coordinates ($E1_X$, $E1_Y$, $E1_Z$), and electrode 96C is located at a position E2 comprising planar coordinates ($E2_X$, $E2_Y$, $E2_Z$).

As depicted in FIGS. 7A-7B, processing circuitry 80 back-calculates a relative location of electrodes 94A, 96A, 96B, and 96C to one another using spatial relationships determined in the manner described above. For example, if all the locations of electrodes 94, 96 and IMB 14 are known, processing circuitry 80 may calculate a relative coordinate of each of electrodes 94, 96 and IMB 14 using the distance equations defined above using a process known as trilateration. Trilateration is the process of determining absolute or relative locations of points by measurement of distances, using the geometry of circles, spheres or triangles.

An example back-calculation algorithm using trilateration is set forth below:

$$\|E_1 - E_0\| = d_{01}$$
$$\|E_2 - E_0\| = d_{02}$$
$$\vdots$$
$$\|E_2 - D\| = d_{D2}$$

The objective of the back-calculation algorithm set forth above is to localize and obtain a relative position of all points (e.g., electrodes 94, 96) using the distances between electrodes 94, 96 determined as described above. For example, using the techniques described above, processing circuitry 80 may determine distances between pairs of electrodes 94, 96, but processing circuitry 80 obtains such distances at different, unknown positions. Processing circuitry 80 may formulate these different distances as an optimization problem, wherein the objective function to be minimized includes the residuals of the distance equations, and wherein the variables in the search space are the coordinates of all the points (e.g., electrodes 94, 96).

Using the back-calculation algorithm set forth above, processing circuitry 80 may determine relative distances between each of electrodes 94A, 96A, 96B, and 96C. For example, as depicted in FIG. 7B, processing circuitry 80 performs back-calculation to determine that electrodes 94A and 96A are a distance $d_{D0}$ apart, electrodes 94A and 96B are a distance $d_{D1}$ apart, electrodes 94A and 96C are a distance $d_{D2}$ apart, electrodes 96A and 96B are a distance $d_{01}$ apart, electrodes 96A and 96C are a distance doe apart, and electrodes 96B and 96C are a distance $d_{12}$ apart.

Figure 8:
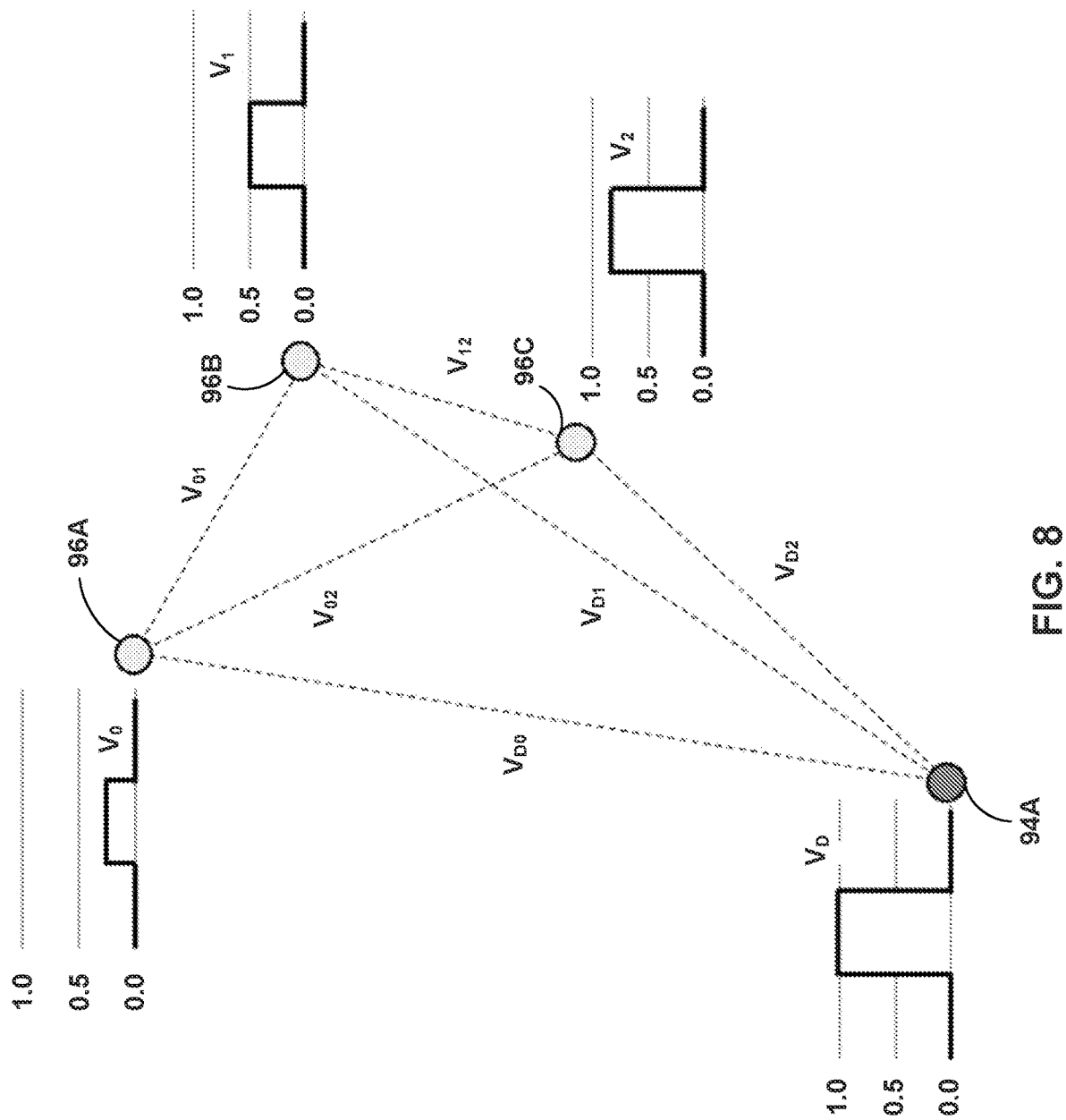
FIG. 8 is a conceptual illustration of example electrodes in accordance with the techniques of the disclosure.

FIG. 8 is a conceptual illustration of example electrodes in accordance with the techniques of the disclosure. For convenience, FIG. 8 is described with respect to IMD 14 of FIG. 2. The techniques described in FIG. 8 may be substantially similar to the techniques for trilateration described in FIGS. 7A-7B above, except that instead of performing trilateration using positions E0, E1, E2, etc., FIG. 8 provides an example of trilateration performed with sensed voltage amplitudes $V_0$, $V_1$, $V_2$, etc.

In accordance with the techniques of the disclosure, a medical device, such as IMD 14 of FIG. 1, senses, via each of a plurality of electrodes 94, 96, a respective electrical signal. In some examples, the electrical signal is an electrical stimulus, as described above. In other examples, the electrical signal is a cardiac signal of a heart of patient 12, stimulation from one or more electrodes 94, etc. IMD 14 determines, for each electrode 94, 96 of the plurality of electrodes 94, 96, a respective value for each respective electrical signal. Further, IMD 14 determines, based on the respective values for each respective electrical signal sensed by each other electrode 94, 96 of the plurality of electrodes 94, 96, a spatial relationship between each electrode 94, 96 of the plurality of electrodes 94, 96 and each other electrode 94, 96 of the plurality of electrodes 94, 96. In this fashion, IMD 14 may determine relative positions of each electrode 94, 96 to each other electrode 94, 96.

IMD 14 may use the sensed electrical signals, such as the sensed cardiac signals of the heart of patient 12, to provide additional context to IMD 14 for use in determining the spatial relationships between each electrode. For example, IMD 14 further determines, based on the respective values for each respective electrical signal sensed by each other electrode 94, 96 of the plurality of electrodes 94, 96, a spatial relationship between each electrode 94, 96 of the plurality of electrodes 94, 96 and the heart of patient 12. In this fashion, IMD 14 may determine an absolute position of each electrode 94, 96 to the heart of patient 12.

In practice, spatial relationships determined by IMD 14, such as a distance d that processing circuitry 80 solves from the equation d=σ×a×I, may have noise compared to a true distance. This noise may arise from a variety of factors. For example, noise may arise due to an accuracy of the impedance measurement (e.g., the capability of IMD 14 to accurately measure impedance). Furthermore, noise may arise due to an accuracy of the conductivity measurement or value stored in memory 82 (e.g., the capability of IMD 14 to accurately measure conductivity, variations in tissue properties between patients, days, a local environment of electrodes 94, 96, etc.). Additionally, by determining only spatial relationships between electrodes 94, 96, processing circuitry 80 may not determine a unique solution for an absolute location of electrodes 94, 96. For example, while processing circuitry 80 determines spatial relationships between each of electrodes 94, 96 to one another, such determined spatial relationships may not define an absolute orientation (e.g., the distances between electrodes 94, 96 may be maintained for different orientations of electrodes 94, 96). However, a unique solution (e.g., an absolute solution to the location and orientation of electrodes 94, 96) is not necessary to determine whether relative movement between electrodes 94, 96 has occurred (e.g., due to lead migration, changes in electrode distance, etc.).

In the context of electrical signals, one may assume that a difference in a sensed signal (e.g., a voltage difference) on each electrode 94, 96 in response to a source signal to be an analogue for the distance d between the electrode 94, 96 and the origin of the source signal. As described herein, the source signal is typically an electrical stimulus delivered via one of electrodes 94, 96. However, in other examples, the source signal may be, e.g., a cardiac signal sensed from a heart of the patient, stimulation from one or more electrodes 94, 96 (e.g., implantable electrodes), one or more electrodes external to the patient, or some other electrical signal that each of electrodes 94, 96 may sense and that varies between the contacts. The use of an electrical stimulus, such as a cardiac signal (or stimulation delivered via electrodes external to the patient applied at known anatomical landmarks) may provide further context to the spatial relationships of electrodes 94, 96 and leads 16 to each other of electrodes 94, 96 and leads 16. Additionally, such electrical stimulus, delivered from a known location (e.g., the heart or external electrodes at known locations) may assist IMD 14 to define spatial relationship between electrodes 94, 96 and leads 16 and the heart of patient 12. Such information may allow processing circuitry 80 to determine spatial relationships of electrodes 94, 96 and leads 16 relative to an anatomical landmark, such as the heart of the patient, rather than merely a relative spatial relationship of electrodes 94, 96 and leads 16 to one another.

For example, as depicted in the example of FIG. 8, electrode 94A delivers an electrical stimulus comprising a voltage amplitude VD. Electrode 96A senses an electrical signal comprising a voltage amplitude $V_0$ resulting from the stimulus, electrode 96B senses an electrical signal comprising a voltage amplitude $V_1$ resulting from the stimulus, and electrode 96C senses an electrical signal comprising a voltage amplitude $V_2$ resulting from the stimulus. Accordingly, a voltage difference $V_{XY}$ between a first voltage $V_X$ and a second voltage $V_Y$ (where $V_X$ and $V_Y$ are the voltages at respective electrodes) may be defined for each electrode 94, 96 as follows:

$$|v_1 - v_0| = v_{01}$$
$$|v_2 - v_0| = v_{02}$$
$$\vdots$$
$$|v_2 - v_D| = v_{D2}$$

Accordingly, processing circuitry 80 determines that a voltage difference Vero exists between electrodes 94A and 96A, a voltage difference $V_{D1}$ exists between electrodes 94A and 96B, a voltage difference $V_{D2}$ exists between electrodes 94A and 96C, a voltage difference $V_{01}$ exists between electrodes 96A and 96B, a voltage difference $V_{01}$ exists between electrodes 96A and 96C, and a voltage difference $V_{12}$ exists between electrodes 96B and 96C.

Processing circuitry 80 may use this additional information in the back calculation algorithm described above to better localize and obtain relative spatial relationships, as well as to better inform the determination of electrode spacing. For example, processing circuitry 80 may use this information to determine a relative and/or absolute position of all points (e.g., electrodes 94, 96). For example, processing circuitry 80 simultaneously uses both the determined distance $d_{XY}$ and the determined voltage difference $V_{XY}$ for each pair of electrodes 94, 96 to scale the electrical distance analogues by a corresponding factor for a largest calculated distance d. For example, processing circuitry may apply the equation $V_{D0} \times f = d_{D0}$, where f is a scaling factor to be applied to all electrical distance analogues V to increase the accuracy of the determined distances d between electrodes 94, 96.

In other examples, processing circuitry 80 simultaneously uses both the determined distance $d_{XY}$ and the determined voltage difference $V_{XY}$ for each pair of electrodes 94, 96 to standardize the spatial relationships between electrodes 94, 96, normalize the spatial relationships between electrodes 94, 96, etc.

In examples where the electrical stimulus is a cardiac signal sensed from a heart of patient 12, the heart has a known, fixed position within the body of patient 12. IMD 14 may therefore use the determined distance $d_{XY}$ and the determined voltage difference $V_{XY}$ for each pair of electrodes 94, 96 to determine spatial relationships between each pair of electrodes 94, 96, such that IMB 14 may determine relative positions of each electrode 94, 96 to each other electrode 94, 96. Furthermore, IMB 14 may use the determined distance $d_{XY}$ and the determined voltage difference $V_{XY}$ for each pair of electrodes 94, 96 to determine spatial relationships between each pair of electrodes 94, 96 and the heart of patient 12 so as to determine absolute positions of each electrode 94, 96 to each other electrode 94, 96 within the body of patient 12.

The following examples are described herein.

Example 1. A method comprising: controlling, by processing circuitry of a medical device, stimulation generation circuitry to deliver, via a first electrode of a plurality of electrodes, an electrical stimulus; sensing, by sensing circuitry and for each other electrode of the plurality of electrodes, a respective electrical signal indicative of the electrical stimulus; determining, by the processing circuitry and for each other electrode, a respective value for each respective electrical signal; and determining, by the processing circuitry, and based on the respective values for each respective electrical signal sensed by each other electrode of the plurality of electrodes, spatial relationships between the first electrode and each other electrode of the plurality of electrodes.

Example 2. The method of example 1, further comprising: selecting, by the processing circuitry and based on the spatial relationships between the first electrode and each other electrode of the plurality of electrodes, at least one electrode of the plurality of electrodes; and controlling, by the processing circuitry, the stimulation generation circuitry to deliver, via the selected at least one electrode, electrical stimulation therapy to the patient.

Example 3. The method of any of examples 1 through 2, further comprising: selecting, by the processing circuitry and based on the spatial relationships between the first electrode and each other electrode of the plurality of electrodes, at least one electrode of the plurality of electrodes; and sensing, by the processing circuitry and via the selected at least one electrode, at least one biosignal of the patient.

Example 4. The method of any of examples 1 through 2, wherein controlling the stimulation generation circuitry to deliver the electrical stimulus comprises controlling the stimulation generation circuitry to deliver an electrical stimulus defined by a first voltage amplitude value; wherein sensing, for each other electrode of the plurality of electrodes, the respective electrical signal indicative of the electrical stimulus comprises sensing, for each other electrode of the plurality of electrodes, electrical signals indicative of second voltage amplitude values indicative of the electrical stimulus, and wherein determining the spatial relationships between the first electrode and each other electrode of the plurality of electrodes comprises determining, based on the first voltage amplitude value and the electrical signals indicative of the second voltage amplitude values, the spatial relationships between the first electrode and each other electrode of the plurality of electrodes.

Example 5. The method of any of examples 1 through 2, wherein determining, based on the respective values for each respective electrical signal sensed by each other electrode of the plurality of electrodes, the spatial relationships between the first electrode and each other electrode of the plurality of electrodes comprises: determining, based on a respective values for a respective electrical signal sensed by a second electrode and a value of a tissue conductivity of a tissue of a patient interposed between the first electrode and the second electrode, a spatial relationship between the first electrode and the second electrode.

Example 6. The method of example 5, further comprising: sensing, by the sensing circuitry, a value of an impedance between the first electrode and the second electrode of the plurality of electrodes; determining, by the processing circuitry and based on the sensed value of the impedance, a type of a tissue interposed between the first electrode and the second electrode, and determining, by the processing circuitry and based on the type of the tissue interposed between the first electrode and the second electrode, the value of the tissue conductivity of the tissue of the patient interposed between the first electrode and the second electrode.

Example 7. The method of any of examples 5 through 6, wherein the type of the tissue interposed between the first electrode and the second electrode is one of a nerve tissue, a bone tissue, a connective tissue, or an adipose tissue.

Example 8. The method of any of examples 1 through 7, further comprising outputting, by the processing circuitry and for display to a user, a representation of the plurality of electrodes depicting a spatial relationship between at least two of the plurality of electrodes.

Example 9. The method of example 8, wherein the representation of the plurality of electrodes depicting the spatial relationship between at least two of the plurality of electrodes comprises a representation of the plurality of electrodes depicting the spatial relationship between at least two of the plurality of electrodes in 3 dimensions.

Example 10. The method of any of examples 1 through 9, wherein the spatial relationships between the first electrode and each other electrode of the plurality of electrodes comprise distances between the first electrode and each other electrode of the plurality of electrodes.

Example 11. The method of any of examples 1 through 10, wherein the plurality of electrodes are disposed on a plurality of leads.

Example 12. The method of any of examples 1 through 11, wherein the plurality of electrodes are implanted within an epidural space of the patient.

Example 13. The method of any of examples 1 through 12, wherein an implantable medical device comprises the stimulation generation circuitry and the processing circuitry.

Example 14. The method of any of claims 1 through 13, further comprising: sensing, by the sensing circuitry and for each electrode of the plurality of electrodes, a respective second electrical signal indicative of a cardiac signal of a heart of a patient; determining, by the processing circuitry and for each electrode of the plurality of electrodes, a respective second value for each respective electrical signal; and determining, by the processing circuitry and based on the respective second values for each respective second electrical signal sensed by each electrode of the plurality of electrodes, a spatial relationship between each electrode of the plurality of electrodes and the heart of the patient.

Example 15. A medical device system comprising: stimulation generation circuitry configured to deliver electrical stimulation via a first electrode of a plurality of electrodes; and processing circuitry configured to control the stimulation generation circuitry to deliver, via the first electrode, an electrical stimulus; sensing circuitry configured to sense, for each other electrode of the plurality of electrodes, a respective electrical signal indicative of the electrical stimulus; wherein the processing circuitry is further configured to determine, for each other electrode, a respective value for each respective electrical signal, and wherein the processing circuitry is further configured to determine, based on the respective values for each respective electrical signal sensed by each other electrode of the plurality of electrodes, spatial relationships between the first electrode and each other electrode of the plurality of electrodes.

Example 16. The system of example 15, wherein the processing circuitry is further configured to: select, based on the spatial relationships between the first electrode and each other electrode of the plurality of electrodes, at least one electrode of the plurality of electrodes; and control the stimulation generation circuitry to deliver, via the selected at least one electrode, electrical stimulation therapy to the patient.

Example 17. The system of any of examples 15 through 16, wherein to determine, based on the respective values for each respective electrical signal sensed by each other electrode of the plurality of electrodes, the spatial relationships between the first electrode and each other electrode of the plurality of electrode, the processing circuitry is configured to: determine, based on a respective values for a respective electrical signal sensed by a second electrode and a value of a tissue conductivity of a tissue of a patient interposed between the first electrode and the second electrode, a spatial relationship between the first electrode and the second electrode.

Example 18. The system of any of examples 15 through 17, further comprising an external programmer configured to output, for display to a user, a representation of the plurality of electrodes depicting a spatial relationship between at least two of the plurality of electrodes.

Example 19. The system of any of examples 15 through 18, wherein the plurality of electrodes are disposed on a plurality of leads.

Example 20. The system of any of examples 15 through 19, wherein an implantable medical device comprises the stimulation generation circuitry, the processing circuitry, and the sensing circuitry.

Example 21. The system of any of examples 15 through 20, wherein the sensing circuitry is further configured to sense, for each electrode of the plurality of electrodes, a respective second electrical signal indicative of a cardiac signal of a heart of a patient, wherein the processing circuitry is further configured to determine, for each electrode of the plurality of electrodes, a respective second value for each respective electrical signal, and wherein the processing circuitry is further configured to determine, based on the respective second values for each respective second electrical signal sensed by each electrode of the plurality of electrodes, a spatial relationship between each electrode of the plurality of electrodes and the heart of the patient.

Example 22. A non-transitory computer-readable medium comprising instructions that, when executed, are configured to cause processing circuitry of a medical device to: control stimulation generation circuitry of the medical device to deliver, via a first electrode of a plurality of electrodes, an electrical stimulus; control sensing circuitry to sense, for each other electrode of the plurality of electrodes, a respective electrical signal indicative of the electrical stimulus; determine, for each other electrode, a respective value for each respective electrical signal; and determine, based on the respective values for each respective electrical signal sensed by each other electrode of the plurality of electrodes, spatial relationships between the first electrode and each other electrode of the plurality of electrodes.

Example 23. A method comprising: sensing, by sensing circuitry of a medical device and for each electrode of a plurality of electrodes, a respective electrical signal indicative of a cardiac signal of a heart of a patient; determining, by the processing circuitry and for each electrode of the plurality of electrodes, a respective value for each respective electrical signal; and determining, by the processing circuitry, and based on the respective values for each respective electrical signal sensed by each electrode of the plurality of electrodes, a spatial relationship between each electrode of the plurality of electrodes and the heart of the patient.

Example 24. The method of example 23, further comprising: selecting, by the processing circuitry and based on the spatial relationship between each electrode of the plurality of electrodes and the heart of the patient, at least one electrode of the plurality of electrodes; and controlling, by the processing circuitry, stimulation generation circuitry to deliver, via the selected at least one electrode, electrical stimulation therapy to the patient.

Example 25. The method of any of examples 23 through 24, further comprising: selecting, by the processing circuitry and based on the spatial relationship between each electrode of the plurality of electrodes and the heart of the patient, at least one electrode of the plurality of electrodes; and sensing, by the processing circuitry and via the selected at least one electrode, at least one biosignal of the patient.

Example 26. The method of examples 23 through 25, further comprising: controlling, by the processing circuitry, stimulation generation circuitry to deliver, via a first electrode of the plurality of electrodes, an electrical stimulus; sensing, by the sensing circuitry and for each other electrode of the plurality of electrodes, a respective second electrical signal indicative of the electrical stimulus; determining, by the processing circuitry and for each other electrode, a respective second value for each respective second electrical signal; and determining, by the processing circuitry, and based on the respective second values for each respective second electrical signal sensed by each electrode of the plurality of electrodes, spatial relationships between the first electrode and each other electrode of the plurality of electrodes.

Example 27. A medical device system comprising: sensing circuitry of a medical device configured to sense, for each electrode of a plurality of electrodes, a respective electrical signal indicative of a cardiac signal of a heart of a patient; and processing circuitry configured to: determine, for each electrode of the plurality of electrodes, a respective value for each respective electrical signal; and determine, based on the respective values for each respective electrical signal sensed by each other electrode of the plurality of electrodes, a spatial relationship between each electrode of the plurality of electrodes and the heart of the patient.

Example 28. The system of example 27, wherein the processing circuitry is further configured to: select, based on the spatial relationship between each electrode of the plurality of electrodes and the heart of the patient, at least one electrode of the plurality of electrodes; and control the stimulation generation circuitry to deliver, via the selected at least one electrode, electrical stimulation therapy to the patient.

Example 29. The system of any of examples 27 through 28, wherein the processing circuitry is further configured to: select, based on the spatial relationship between each electrode of the plurality of electrodes and the heart of the patient, at least one electrode of the plurality of electrodes; and control, by the processing circuitry, the sensing circuitry to sense, via the selected at least one electrode, at least one biosignal of the patient.

Example 30. The system of any of examples 27 through 29, wherein the processing circuitry is further configured to control the stimulation generation circuitry to deliver, via a first electrode of the plurality of electrodes, an electrical stimulus, wherein the sensing circuitry is further configured to sense, for each other electrode of the plurality of electrodes, a respective second electrical signal indicative of the electrical stimulus, wherein the processing circuitry is further configured to determine, for each other electrode, a respective second value for each respective second electrical signal, and wherein the processing circuitry is further configured to determine, based on the respective second values for each respective second electrical signal sensed by each other electrode of the plurality of electrodes, spatial relationships between the first electrode and each other electrode of the plurality of electrodes.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
   sensing, by sensing circuitry of a medical device and via each electrode of a plurality of electrodes implanted within an epidural space of a patient, a respective electrical signal indicative of a cardiac signal of a heart of the patient;
   determining, by processing circuitry and for each electrode of the plurality of electrodes implanted within the epidural space, a respective value for each respective electrical signal; and
   determining, by the processing circuitry, and based on the respective values for each respective electrical signal sensed by each electrode of the plurality of electrodes, a spatial relationship between each electrode of the plurality of electrodes implanted within the epidural space and each other electrode of the plurality of electrodes.

2. The method of claim 1, further comprising:
   selecting, by the processing circuitry and based on the spatial relationship between each electrode of the plurality of electrodes and each other electrode of the plurality of electrodes, at least one electrode of the plurality of electrodes; and
   controlling, by the processing circuitry, stimulation generation circuitry to deliver, via the selected at least one electrode, electrical stimulation therapy to the patient.

3. The method of claim 1, further comprising:
   selecting, by the processing circuitry and based on the spatial relationship between each electrode of the plurality of electrodes and each other electrode of the plurality of electrodes, at least one electrode of the plurality of electrodes; and sensing, by the processing circuitry and via the selected at least one electrode, at least one biosignal of the patient.

4. The method of claim 1, wherein determining the spatial relationship between each electrode of the plurality of electrodes and each other electrode of the plurality of electrodes comprises:
obtaining a known location of the heart within the patient; and
determining, based on the known location of the heart and the respective values for each respective electrical signal sensed by each electrode of the plurality of electrodes, the spatial relationship between each electrode of the plurality of electrodes and each other electrode of the plurality of electrodes.

5. The method of claim 1, further comprising:
controlling, by the processing circuitry, stimulation generation circuitry to deliver, via a first electrode of the plurality of electrodes, an electrical stimulus;
sensing, by the sensing circuitry and for each other electrode of the plurality of electrodes, a respective second electrical signal indicative of the electrical stimulus;
determining, by the processing circuitry and for each other electrode, a respective second value for each respective second electrical signal; and
determining, by the processing circuitry and based on both the respective second values for each respective second electrical signal sensed by each electrode of the plurality of electrodes and the respective values for each respective electrical signal indicative of the cardiac signal, the spatial relationships between the first electrode and each other electrode of the plurality of electrodes.

6. The method of claim 1, further comprising outputting, by the processing circuitry and for display to a user, a representation of the plurality of electrodes depicting the spatial relationship between at least two of the plurality of electrodes.

7. The method of claim 6, wherein the representation of the plurality of electrodes depicting the spatial relationship between at least two of the plurality of electrodes comprises a representation of the plurality of electrodes depicting the spatial relationship between at least two of the plurality of electrodes in 3 dimensions.

8. The method of claim 1, wherein the plurality of electrodes are disposed on a plurality of leads.

9. A medical device system comprising:
sensing circuitry configured to sense, via each electrode of a plurality of electrodes implanted within an epidural space of a patient, a respective electrical signal indicative of a cardiac signal of a heart of a patient; and
processing circuitry configured to:
determine, for each electrode of the plurality of electrodes implanted within the epidural space, a respective value for each respective electrical signal; and
determine, based on the respective values for each respective electrical signal sensed by each other electrode of the plurality of electrodes, a spatial relationship between each electrode of the plurality of electrodes implanted within the epidural space and each other electrode of the plurality of electrodes.

10. The system of claim 9, wherein the processing circuitry is further configured to determine, based on the respective values for each respective electrical signal sensed by each electrode of the plurality of electrodes, a spatial relationship between each electrode of the plurality of electrodes and the heart of the patient.

11. The system of claim 9, wherein the processing circuitry is further configured to:
select, based on the spatial relationship between each electrode of the plurality of electrodes and each other electrode of the plurality of electrodes, at least one electrode of the plurality of electrodes; and
control stimulation generation circuitry to deliver, via the selected at least one electrode, electrical stimulation therapy to the patient.

12. The system of claim 9, wherein the processing circuitry is further configured to:
select, based on the spatial relationship between each electrode of the plurality of electrodes and the heart of the patient, at least one electrode of the plurality of electrodes; and
control, by the processing circuitry, the sensing circuitry to sense, via the selected at least one electrode, at least one biosignal of the patient.

13. The system of claim 9,
wherein the processing circuitry is further configured to control stimulation generation circuitry to deliver, via a first electrode of the plurality of electrodes, an electrical stimulus,
wherein the sensing circuitry is further configured to sense, for each other electrode of the plurality of electrodes, a respective second electrical signal indicative of the electrical stimulus,
wherein the processing circuitry is further configured to determine, for each other electrode, a respective second value for each respective second electrical signal, and
wherein the processing circuitry is further configured to determine, based on both the respective second values for each respective second electrical signal sensed by each other electrode of the plurality of electrodes and the respective values for each respective electrical signal indicative of the cardiac signal, the spatial relationships between the first electrode and each other electrode of the plurality of electrodes.

14. The system of claim 9, further comprising outputting, by the processing circuitry and for display to a user, a representation of the plurality of electrodes depicting the spatial relationship between at least two of the plurality of electrodes.

15. The system of claim 14, wherein the representation of the plurality of electrodes depicting the spatial relationship between at least two of the plurality of electrodes comprises a representation of the plurality of electrodes depicting the spatial relationship between at least two of the plurality of electrodes in 3 dimensions.

16. The system of claim 9, wherein the plurality of electrodes are disposed on a plurality of leads.

17. The system of claim 9, further comprising the plurality of electrodes configured to be implanted within the epidural space of the patient.

18. The system of claim 9, further comprising an implantable medical device comprising stimulation generation circuitry and the processing circuitry.

19. The system of claim 9, wherein the processing circuitry is further configured to:
select, based on the spatial relationship between each electrode of the plurality of electrodes and each other electrode of the plurality of electrodes, a value for at least one stimulation parameter that defines electrical stimulation therapy; and
control stimulation generation circuitry to deliver the electrical stimulation therapy to the patient according to the value for the at least one stimulation parameter.

20. A non-transitory computer-readable medium comprising instructions that, when executed, are configured to cause processing circuitry of a medical device to:
- control sensing circuitry to sense, via each electrode of a plurality of electrodes implanted within an epidural space of a patient, a respective electrical signal indicative of a cardiac signal of a heart of a patient;
- determine, for each electrode of the plurality of electrodes implanted within the epidural space, a respective value for each respective electrical signal; and
- determine, based on the respective values for each respective electrical signal sensed by each other electrode of the plurality of electrodes, a spatial relationship between each electrode of the plurality of electrodes implanted within the epidural space and each other electrode of the plurality of electrodes.

\* \* \* \* \*